(12) United States Patent
Natori et al.

(10) Patent No.: US 7,397,054 B2
(45) Date of Patent: Jul. 8, 2008

(54) PARTICLE BEAM THERAPY SYSTEM AND CONTROL SYSTEM FOR PARTICLE BEAM THERAPY

(75) Inventors: Takayoshi Natori, Chiyoda (JP); Kunio Moriyama, Hitachi (JP); Kazumune Sakai, Hitachiohta (JP); Takahide Nakayama, Nara (JP)

(73) Assignee: Hitachi, Ltd., Tokyo (JP)

( * ) Notice: Subject to any disclaimer, the term of this patent is extended or adjusted under 35 U.S.C. 154(b) by 17 days.

(21) Appl. No.: 11/602,489

(22) Filed: Nov. 21, 2006

(65) Prior Publication Data

US 2007/0176125 A1 Aug. 2, 2007

Related U.S. Application Data

(63) Continuation of application No. 11/188,642, filed on Jul. 26, 2005, now abandoned.

(30) Foreign Application Priority Data

Jul. 28, 2004 (JP) ............................. 2004-220338

(51) Int. Cl.
*A61N 5/00* (2006.01)
*A61N 5/10* (2006.01)
*G21G 1/00* (2006.01)

(52) U.S. Cl. ............ 250/492.3; 250/492.1; 250/492.21; 315/500; 315/503; 315/504

(58) Field of Classification Search ............... 250/492.3
See application file for complete search history.

(56) References Cited

U.S. PATENT DOCUMENTS

| | | | |
|---|---|---|---|
| 4,870,287 A * | 9/1989 | Cole et al. ............... | 250/492.3 |
| 5,039,867 A | 8/1991 | Nishihara et al. | |
| 5,260,581 A * | 11/1993 | Lesyna et al. ............ | 250/492.3 |
| 5,440,133 A | 8/1995 | Moyers et al. | |
| 5,866,912 A | 2/1999 | Slater et al. | |
| 6,034,377 A | 3/2000 | Pu | |
| 6,777,700 B2 | 8/2004 | Yanagisawa et al. | |
| 6,803,591 B2 | 10/2004 | Yamashita et al. | |

(Continued)

FOREIGN PATENT DOCUMENTS

EP 0 986 070 A1 3/2000

(Continued)

*Primary Examiner*—David A. Vanore
*Assistant Examiner*—Bernard Souw
(74) *Attorney, Agent, or Firm*—Dickstein Shapiro LLP

(57) ABSTRACT

A particle beam therapy system comprises a charged particle beam generator for generating a charged particle beam, two or more treatment rooms provided with respective irradiation devices for irradiating the charged particle beam, a beam line for transporting the charged particle beam extracted from the charged particle beam generator to the irradiation device in selected one of the two or more treatment rooms, a beam detection processing/control unit for monitoring a beam state of the charged particle beam in one of the two or more irradiation devices, and a selector for switchably selecting one of the irradiation devices which is to be monitored by the beam detection processing/control unit. The selector is controlled such that the selector establishes connection with the irradiation device in the selected one treatment room to which the charged particle beam is transported through the beam line. The system configuration can be simplified while maintaining the operation efficiency.

20 Claims, 15 Drawing Sheets

U.S. PATENT DOCUMENTS

| | | |
|---|---|---|
| 6,903,356 B2 | 6/2005 | Muramatsu et al. |
| 7,012,267 B2 | 3/2006 | Moriyama et al. |
| 7,026,636 B2 | 4/2006 | Yanagisawa et al. |
| 7,030,396 B2 | 4/2006 | Muramatsu et al. |
| 7,173,264 B2 * | 2/2007 | Moriyama et al. ....... 250/492.3 |
| 7,262,424 B2 * | 8/2007 | Moriyama et al. ....... 250/492.3 |
| 7,319,231 B2 * | 1/2008 | Moriyama et al. ....... 250/492.3 |
| 2004/0000650 A1 | 1/2004 | Yanagisawa et al. |
| 2004/0056212 A1 | 3/2004 | Yanagisawa et al. |
| 2004/0061077 A1 | 4/2004 | Muramatsu et al. |
| 2004/0061078 A1 | 4/2004 | Muramatsu et al. |
| 2004/0118081 A1 | 6/2004 | Reimoser et al. |
| 2004/0149934 A1 | 8/2004 | Yanagisawa et al. |
| 2004/0173763 A1 * | 9/2004 | Moriyama et al. ....... 250/492.1 |
| 2004/0174958 A1 * | 9/2004 | Moriyama et al. .......... 378/145 |
| 2004/0183033 A1 * | 9/2004 | Moriyama et al. ........ 250/492.3 |
| 2004/0200982 A1 | 10/2004 | Moriyama et al. |
| 2005/0139787 A1 * | 6/2005 | Chiba et al. .............. 250/492.3 |
| 2005/0145804 A1 | 7/2005 | Yanagisawa et al. |
| 2006/0022152 A1 * | 2/2006 | Natori et al. ............. 250/493.1 |
| 2006/0113487 A1 * | 6/2006 | Naumann et al. ......... 250/492.3 |
| 2007/0176125 A1 * | 8/2007 | Natori et al. ............. 250/493.1 |

FOREIGN PATENT DOCUMENTS

| | | |
|---|---|---|
| EP | 1 454 654 A2 | 9/2004 |
| JP | 11-501232 | 2/1999 |
| JP | 2004-267481 | 9/2004 |
| WO | WO 96/25201 | 8/1996 |
| WO | WO 2004/101070 A1 | 11/2004 |

* cited by examiner

PARTICLE BEAM THERAPY SYSTEM AND CONTROL SYSTEM FOR PARTICLE BEAM THERAPY

This is a continuation of application Ser. No. 11/188,642, filed Jul. 26, 2005 now abandoned, the entire disclosure of which is incorporated herein by reference.

BACKGROUND OF THE INVENTION

1. Field of the Invention

The present invention relates to a particle beam therapy system in which a charged particle beam of protons or carbon ions is irradiated to the affected part in the body of a patient for treatment, and to a control system for particle beam therapy. More particularly, the present invention relates to a particle beam therapy system having a plurality of treatment rooms, and a control system for such a particle beam therapy system.

2. Description of the Related Art

There is known a therapy method of irradiating a charged particle beam of protons or carbon ions to the affected part in the body of a patient, e.g., the cancer, for treatment. A large-scaled one of therapy systems for use with such a therapy method comprises a charged particle beam generator, a beam line, and a plurality of treatment rooms. A charged particle beam accelerated by the charged particle beam generator reaches, through the beam line, an irradiation device installed in a rotating gantry within one treatment room selected from among the plurality of treatment rooms, and is irradiated to the affected part of the patient body lying on a treatment bed from a nozzle of the irradiation device (see, e.g., Patent Reference 1; JP,A 11-501232).

SUMMARY OF THE INVENTION

Generally, a control system for the above-mentioned known therapy system having a plurality of treatment rooms comprises a central controller for performing supervisory control of the overall therapy system, a treatment planning system in which a treatment plan database is stored, a central interlock device for stopping the irradiation, e.g., when any abnormality is detected, an accelerator controller for controlling extraction and stop of a charged particle beam from the charged particle beam generator, a magnet power supply controller for performing power supply control for magnets disposed in predetermined positions within the charged particle beam generator and the beam line, various controllers installed in each of the treatment rooms, and a monitoring function device installed in each of the treatment rooms and monitoring the state of the charged particle beam being irradiated from the irradiation device.

The controllers installed in each of the treatment rooms include a gantry controller for controlling the rotation of a rotating gantry, a bed controller for controlling the movement of a treatment bed, irradiation nozzle controllers for controlling those units of equipment mounted in the irradiation device which are used for forming an irradiation field, such as an SOBP forming device and a bolus collimator, and an irradiation controller for controlling the gantry controller, the bed controller and the irradiation nozzle controllers in a supervisory manner.

The monitoring function device installed in each of the treatment rooms has not only the function of determining whether the beam state during irradiation is within a preset allowable range, thereby detecting an abnormality if the beam state is outside the allowable range, but also the function of determining whether the dose has reached a preset value, thereby detecting attainment of the target dose when the dose has reached the preset value. When an abnormality of the dose attainment is detected by the monitoring function device, the beam extraction from the charged particle beam generator is stopped.

In the therapy system having a plurality of treatment rooms, the charged particle beam extracted from the charged particle beam generator is usually irradiated in only one of the treatment rooms and is never irradiated in the plurality of treatment rooms at the same time. Taking into account that usual situation, it is conceivable to employ the controllers and the monitoring function device, which have been so far installed in each treatment room, in common with the plurality of treatment rooms instead of installing them in each treatment room. More specifically, in the therapy system having a plurality of treatment rooms, the therapy is generally progressed such that the irradiation is performed in one selected treatment room, while positioning of the patient, setting of the irradiation field forming equipment in the irradiation device, etc. are performed in the next treatment room. It is therefore can be said that the gantry controller for controlling the rotation of the rotating gantry, the bed controller for controlling the movement of the treatment bed, the irradiation nozzle controllers for controlling the irradiation field forming equipment mounted in the irradiation device, and the irradiation controller for controlling those controllers in a supervisory manner are preferably installed in each of the treatment rooms in consideration of the operation efficiency of the therapy system. On the other hand, of the above-mentioned units installed in each treatment room, the monitoring function device for monitoring the beam state is not necessarily required to be installed in each treatment room because it serves to monitor the beam state during irradiation and is not used in the other treatment rooms than that under irradiation. Also, the monitoring function device does not take part in the positioning of the patient and setting of the irradiation field forming equipment. Accordingly, sharing the monitoring function device by a plurality of treatment rooms will not lead to a reduction in the operation efficiency of the therapy system.

Thus, the known therapy system is still susceptible to simplification because of having a control system configured such that the monitoring function device for monitoring the beam state during irradiation is installed in each treatment room in spite of being sharable by a plurality of treatment rooms.

In view of the above-mentioned problem with the related art, an object of the present invention is to provide a particle beam therapy system and a control system for particle beam therapy, which can simplify a system configuration while maintaining the operation efficiency.

To achieve the above object, the present invention provides a particle beam therapy system for irradiating a charged particle beam to an affected part of the body for treatment, wherein the therapy system comprises a charged particle beam generator for generating the charged particle beam; irradiation devices installed respectively in a plurality of treatment rooms and irradiating the charged particle beam; a beam line for transporting the charged particle beam extracted from the charged particle beam generator to the irradiation device in selected one of the plurality of treatment rooms; a monitoring unit for monitoring a beam state of the charged particle beam in one of the irradiation devices; a selector for switchably selecting one of the irradiation devices which is to be monitored by the monitoring unit; and a first control unit for controlling the selector such that the selector establishes connection with the irradiation device in the selected one of the plurality of treatment rooms to which the charged particle beam is transported through the beam line.

With those features, since the irradiation device to be monitored by the monitoring unit is selected by the selector in a switching manner and the first control unit controls the selector such that the selector establishes connection with the irradiation device in the selected one of the plurality of treatment rooms to which the charged particle beam is transported through the beam line, the monitoring unit can be shared by a plurality of treatment rooms. As a result, the system configuration can be simplified.

According to the present invention, it is possible to simplify the system configuration while maintaining the operation efficiency.

Figure 1:
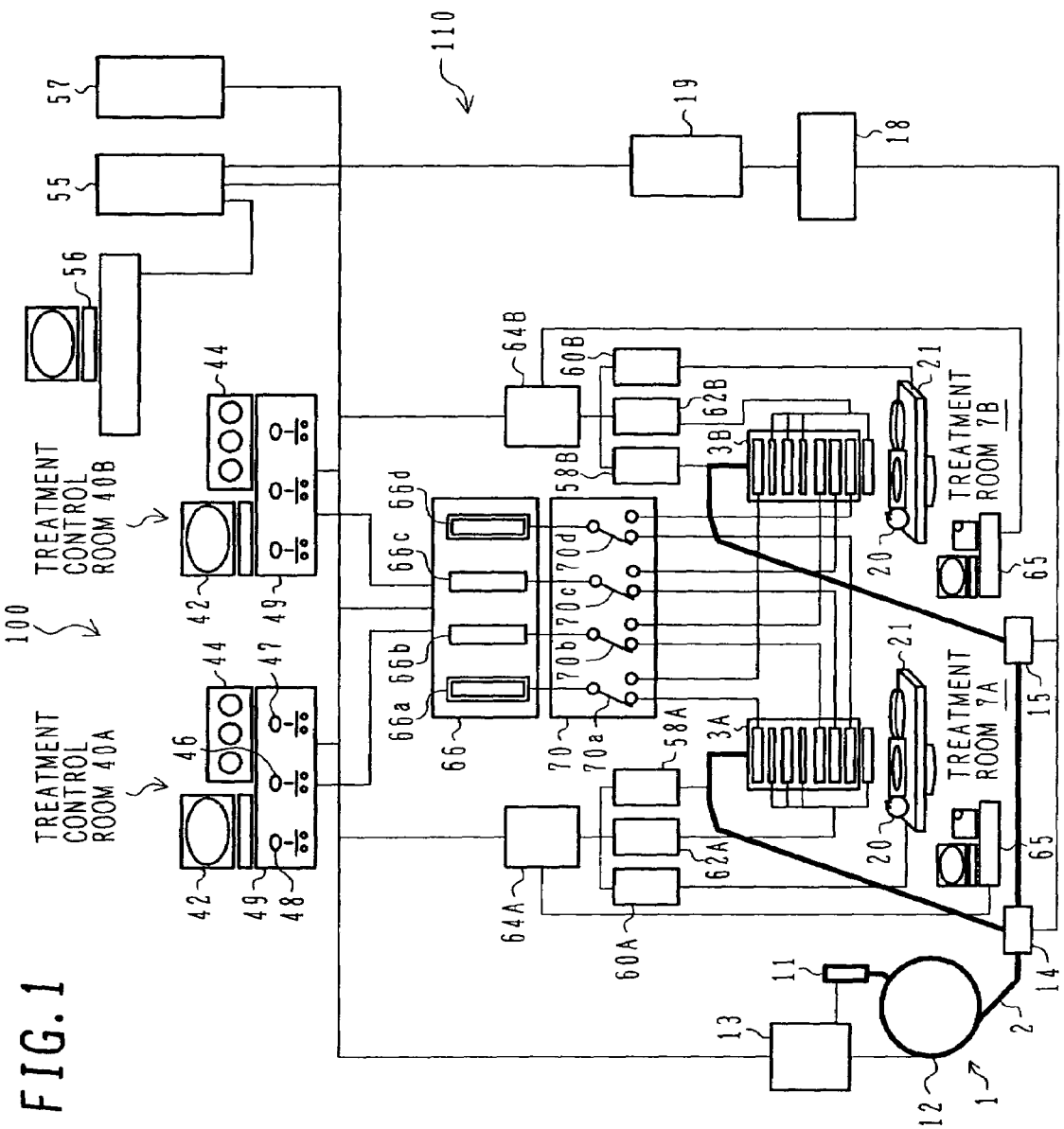
FIG. 1 is an overall block diagram of a particle beam therapy system according to a first embodiment of the present invention.

REFERENCE NUMERALS 1 charged particle beam generator
2 beam line
3A,3B irradiation device
4A,4B irradiation device
7A,7B treatment room
8A,8B treatment room
19 power supply controller (beam line controller)
25,33 profile monitor (detector)
29 energy monitor (detector)
30 flatness monitor (detector)
31,38 dose monitor (detector)
34,35 scanning magnets
37 spot position monitor (detector)
42 display monitor (display)
44 operating/monitoring panel (display)
55 central controller (determining unit)
57 central interlock device (second control unit and third control unit)
66 beam detection processing/control unit (monitoring unit, first control unit, and determining unit)
67 beam detection processing/control unit (monitoring unit, first control unit, determining unit, and scan stroke control unit)
70,71 selector
100 particle beam therapy system
110 control system
135 beam detection processing/control unit (monitoring unit, first control unit, and determining unit)
136 beam detection processing/control unit (monitoring unit, first control unit, determining unit, and scan stroke control unit)
137 beam detection processing/control unit (monitoring unit, first control unit, and determining unit)
140 selector
300 particle beam therapy system
310 control system
400 particle beam therapy system
410 control system
600 particle beam therapy system
610 control system

DESCRIPTION OF THE PREFERRED EMBODIMENTS

Embodiments of the present invention will be described in detail below with reference to the drawings.

First Embodiment

A particle beam therapy system according to one preferred embodiment of the present invention will be described as a first embodiment with reference to FIG. 1. In the illustrated practical form, a particle beam therapy system 100 of this first embodiment is constructed as a proton beam therapy system. The particle beam therapy system 100 comprises a charged particle beam generator 1, a beam line 2 connected to the charged particle beam generator 1 and extending downstream from it, and a plurality (two in this embodiment) of treatment rooms 7A, 7B. A plurality (two in this embodiment) of irradiation devices (i.e., irradiation field forming devices) 3A, 3B are installed in the treatment rooms 7A, 7B in one-to-one relation.

The charged particle beam generator 1 comprises an ion source (not shown), a pre-stage accelerator (e.g., a linear accelerator) 11, and a synchrotron 12 as a main accelerator. Ions (e.g., protons (or carbon ions)) generated in the ion source are accelerated by the pre-stage accelerator 11, and an ion beam (charged particle beam) exiting the pre-stage accelerator 11 enters the synchrotron 12. The ion beam having entered the synchrotron 12 circulates within the synchrotron 12, and after being accelerated to a preset level of energy (e.g., 100-200 MeV), the ion beam is extracted from the synchrotron 12. Operations of the prestage accelerator 11 and the synchrotron 12 are controlled by an accelerator controller 13.

The ion beam extracted from the synchrotron 12 is transported to selected one of the treatment rooms 7A, 7B through the beam line 2. The beam line 2 includes switching magnets (bending magnets) 14, 15. The ion beam introduced to the beam line 2 is selectively transported to one of the treatment rooms 7A, 7B depending on the presence or absence of a bending action that is effectuated with switching-over between excitation and non-excitation of the switching magnets 14, 15. Numeral 18 denotes a magnet power supply for making switching-over between excitation and non-excitation of various magnets in the beam line 2, including the switching magnets 14, 15, and 19 denotes a power supply controller (beam line controller) for controlling the magnet power supply 18.

A downstream end of the beam line 2 on the treatment room side is connected to each of the irradiation devices 3A, 3B mounted to respective rotating gantries (not shown) which are installed in the treatment rooms 7A, 7B. In each of the treatment rooms 7A, 7B, a patient 20 is lying on a treatment bed 21 positioned in a treatment cage (not shown) that is formed inside the rotating gantry. The ion beam exiting the irradiation device 3A or 3B is irradiated to the affected part (not shown) in the body of the patient 20.

Figure 2:
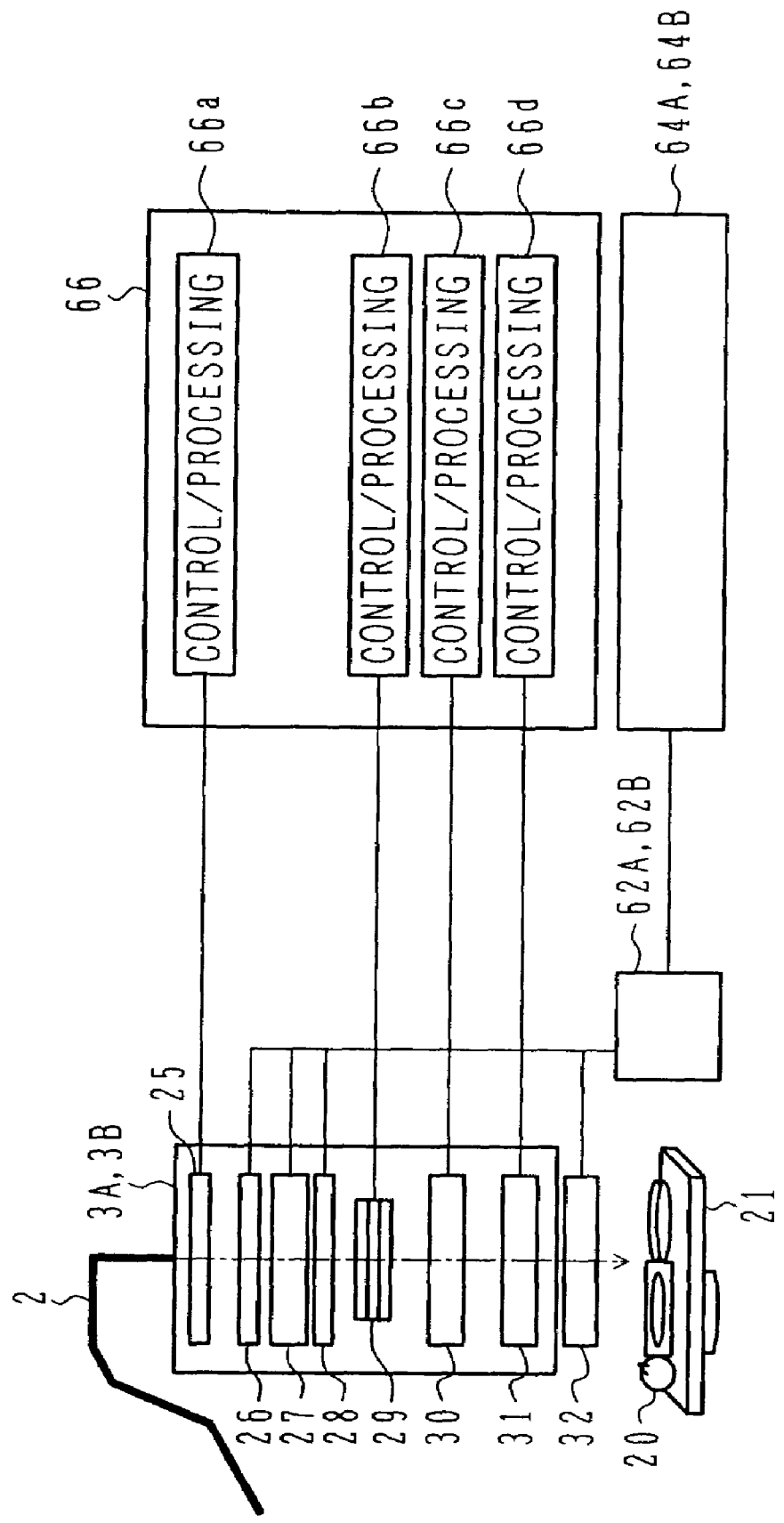
FIG. 2 is a schematic view showing a general equipment configuration of an irradiation device of the passive irradiation type shown in FIG. 1.

The irradiation devices 3A, 3B are each of the passive irradiation type in which the ion beam is scattered by a scatterer and the scattered ion beam is shaped by a collimator in match with the shape of the affected part (cancer) in the patient body, followed by irradiation to the cancer. FIG. 2 schematically shows a general equipment configuration of each of the irradiation devices 3A, 3B.

As shown in FIG. 2, each of the passive irradiation devices 3A, 3B includes a profile monitor (detector) 25 for measuring the centroid and width of the ion beam entering the irradiation device 3A, 3B from the beam line 2, a first scatterer 26 for scattering the beam, an SOBP (Spread-Out Bragg Peak) forming device (e.g., a ridge filter or a range modulation wheel) 27, a second scatterer 28, an energy monitor (detector) 29 for measuring an energy amount of the irradiation beam, a flatness monitor (detector) 30 for measuring uniformity of the irradiated beam in a direction perpendicular to the direction of travel of the beam, a dose monitor (detector) 31 for detecting the dose, and a bolus collimator 32 for adjusting the range of the ion beam and the shape of an irradiation field in the direction perpendicular to the direction of travel of the beam to be matched with a target shape. Those units 25 to 32 are mounted in the irradiation device in the mentioned order from the upstream side in the direction of travel of the beam.

Returning to FIG. 1, treatment control rooms 40A, 40B where the operations necessary for the treatment, etc. are carried out are installed respectively near the treatment rooms 7A, 7B. Each of the treatment control rooms 40A, 40B includes a display monitor (display unit) 42 and an operating/monitoring panel (display unit) 44 which are used to display the treatment situation and beam information of the ion beam, such as the dose, and also includes a console 49 provided with an irradiation start button 46 for starting the irradiation, an irradiation stop button 47 for stopping the irradiation, and a beam request button 48 for issuing a request for the beam irradiation to the charged particle beam generator 1.

A control system 110 provided in the particle beam therapy system 100 of this embodiment will be described below.

The control system 110 comprises a central controller (determining unit) 55 for performing supervisory control of the entirety of the therapy system 100, a treatment planning system 56 in which a treatment plan database is stored, a central interlock device (second control unit and third control unit) 57 for stopping the irradiation, e.g., when any abnormality of the beam is detected in the irradiation devices 3A, 3B, an accelerator controller 13 for performing control of the synchrotron 12, and the above-mentioned power supply controller 19 for controlling a power supply for the magnets in the beam line 2.

Furthermore, the control system 110 includes, in the treatment rooms 7A, 7B in one-to-one relation, gantry controllers 58A, 58B, bed controllers 60A, 60B, irradiation nozzle controllers 62A, 62B, and irradiation controllers 64A, 64B for controlling those corresponding three controllers in a supervisory manner. In each treatment room 7A, 7B, the rotating gantry is rotated by controlling the rotation of a motor (not shown) by the gantry controller 58A, 58B, and the treatment bed 21 is moved and controlled by the bed controller 60A, 60B. Also, of the equipment mounted in each irradiation device 3A, 3B, those units for forming the irradiation field, such as the first and second scatterers 26, 28, the SOBP forming device 27 and the bolus collimator 32, are controlled by the irradiation nozzle controller 62A, 62B.

More specifically, when positioning the patient 20, a doctor (or an operator) standing near the patient 20 in each treatment room 7A, 7B manipulates a nearby operating unit (e.g., a pendant) 65 connected to the irradiation controller 64A, 64B, whereupon a control start signal or a control stop signal is transmitted to corresponding one of the above-mentioned three controllers through the irradiation controller 64A, 64B. For example, when the control start signal for the rotating gantry is outputted from the nearby operating unit 65 in the treatment room 7A, the central controller 55 takes in rotational angle information for the rotating gantry with regards to the patient 20 from the treatment plan information stored in the treatment planning system 56 and transmits the taken-in rotational angle information to the gantry controller 58A through the irradiation controller 64A. The gantry controller 58A rotates the rotating gantry based on the rotational angle information.

In addition, the control system 110 comprises a beam detection processing/control unit (monitoring unit, first control unit and determining unit) 66 for both the treatment rooms 7A, 7B. The functions of the beam detection processing/control unit 66 will be described below with reference to FIG. 2.

As shown in FIG. 2, of the equipment mounted in each passive irradiation device 3A, 3B, those units for forming the irradiation field, i.e., the first and second scatterers 26, 28, the SOBP forming device 27, and the bolus collimator 32, are controlled by the irradiation nozzle controller 62A, 62B. Because those units are mounted in match with the irradiation target for each patient, the irradiation nozzle controller 62A, 62B makes monitoring to avoid a possibility that a false unit is mounted.

On the other hand, the beam information obtained from those detectors among the equipment mounted in the irradiation device 3A, 3B which are used to detect the beam information of the ion beam under irradiation, i.e., the profile monitor 25, the energy monitor 29, the flatness monitor 30, and the dose monitor 31, is taken into the beam detection processing/control unit 66. The beam detection processing/control unit 66 has the functions of monitoring the beam information obtained by those detectors. More specifically, the beam detection processing/control unit 66 includes a control/processing section 66a for taking in the information measured by the profile monitor 25, computing the centroid and width of the ion beam, and detecting an abnormality of the centroid or width when the computed result exceeds an allowable value, a control/processing section 66b for computing an energy distribution from the information measured by the energy monitor 29 and detecting an abnormality of the energy distribution when the computed result exceeds an allowable value, a control/processing section 66c for computing flatness of the ion beam from the information measured by the flatness monitor 30 and detecting an abnormality of the beam flatness when the computed result exceeds an allowable value, and a control/processing section 66d for monitoring the dose from the information measured by the dose monitor 31 and detecting attainment of the target dose when the monitored does has reached a preset value.

When any beam abnormality is detected by the thus-constructed beam detection processing/control unit 66 (exactly speaking, by the control/processing sections 66a to 66c), the beam detection processing/control unit 66 outputs an abnormality signal to the central interlock device 57, and the central interlock device 57 having received the abnormality signal outputs an irradiation stop signal to the accelerator controller 13. Then, an on/off switch (not shown) provided in the synchrotron 12 is opened under control of the accelerator controller 13, whereupon the supply of RF waves to an RF knock-out electrode (not shown) is stopped and the extraction of the ion beam from the synchrotron 12 is also stopped. When the attainment of the target dose is detected by the beam detection processing/control unit 66 (exactly speaking, by the control/processing section 66d), the beam detection processing/control unit 66 outputs a dose attainment signal to the central controller 55, and the central controller 55 having received the dose attainment signal outputs a beam irradiation end signal to the accelerator controller 13, whereby the extraction of the ion beam from the synchrotron 12 is stopped in the same way as that described above. As a result, excess irradiation and false irradiation to the patient 20 can be avoided.

The control system 110 includes one beam detection processing/control unit 66 for the two irradiation devices 3A, 3B, and one of those two irradiation devices from which the beam detection processing/control unit 66 obtains the beam information (i.e., the irradiation device as a monitoring target) is selected by a selector 70. In other words, the beam detection processing/control unit 66 is shared by the irradiation devices 3A, 3B (or the treatment rooms 7A, 7B).

The selector 70 includes a switching circuit 70a for switching over the profile monitors 25, 25 of the irradiation devices 3A, 3B, a switching circuit 70b for switching over the energy monitors 29, 29 of the irradiation devices 3A, 3B, a switching circuit 70c for switching over the flatness monitors 30, 30 of the irradiation devices 3A, 3B, and a switching circuit 70d for switching over the dose monitors 31, 31 of the irradiation devices 3A, 3B. Those switching circuits 70a to 70d are all always turned to the same side when switched over, without being irregularly turned to the different sides.

Figure 3:
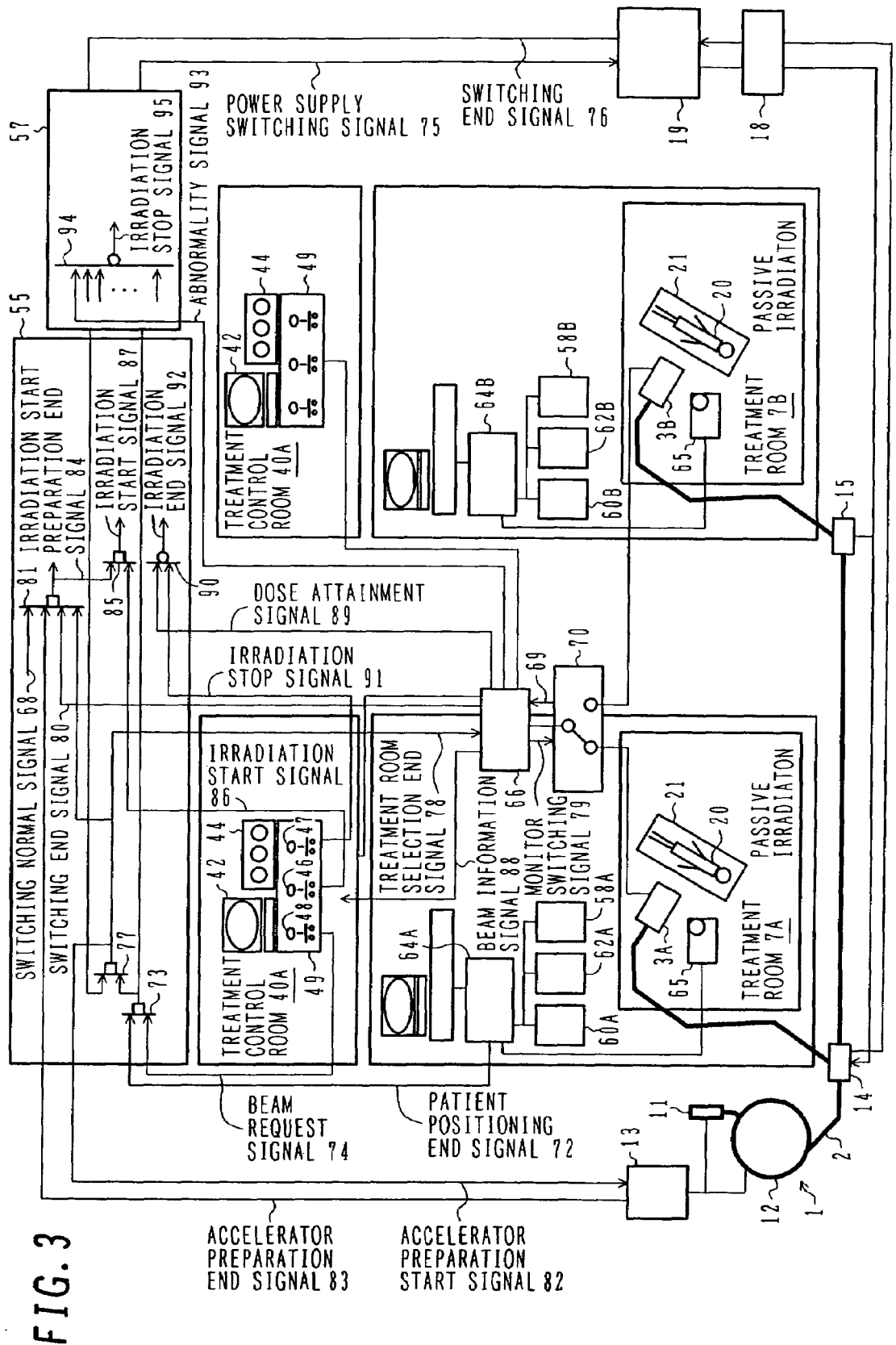
FIG. 3 is a block diagram showing a flow of control signals in a control system during operation of the particle beam therapy system according to the first embodiment of the present invention.

The switching operation of the selector 70 is performed by the beam detection processing/control unit 66 (more exactly speaking, the switching circuits 70a to 70d of the selector 70 are switched by the control/processing sections 66a to 66d of the beam detection processing/control unit 66, respectively) so as to establish connection with the selected treatment room (i.e., the treatment room to which the ion beam is transported through the beam line 2). The switching sequence will be described below with reference to FIG. 3. FIG. 3 is a block diagram showing a flow of control signals in a control system 110 during operation of the particle beam therapy system 100 according to this embodiment. In the following description, it is assumed that the treatment room 7A is the selected treatment room (i.e., the treatment room where the irradiation for treatment is performed).

Using the nearby operating unit 65, a doctor (or an operator) makes positioning of the patient 20 by driving the rotating gantry and the treatment bed 21 under control of the gantry controller 58A and the bed controller 60A through the irradiation controller 64A, and also makes setting of the equipment in the irradiation device 3A, i.e., the first and second scatterers 26, 28, the SOBP forming device 27, and the bolus collimator 32, under control of the irradiation nozzle controller 62A. Upon completion of the patient positioning and the equipment setting, the irradiation controller 64A outputs a patient positioning end signal 72 to an AND circuit 73 in the central controller 55. On the other hand, when a doctor (or an operator) in the treatment control room 40A operates a beam request button 48 on the console 49, a beam request signal 74 is outputted from the console 49 to the AND circuit 73 in the central controller 55.

When the patient positioning end signal 72 and the beam request signal 74 are both inputted to the AND circuit 73 and the AND logical condition is satisfied, the AND circuit 73 outputs a power supply switching signal 75 to the power supply controller 19. Responsively, the power supply controller 19 switches over the power supply for the switching magnet 14 in the beam line 2 through the magnet power supply 18. As a result, a beam path toward the treatment room 7A is formed, whereby the selection of the treatment room is completed. Upon completion of the selection of the treatment room, the power supply controller 19 outputs a switching end signal 76 to an AND circuit 77 in the central controller 55.

When the switching end signal 76 and the power supply switching signal 75 from the AND circuit 73 are both inputted to the AND circuit 77 and the AND logical condition is satisfied, the AND circuit 77 outputs a treatment room selection end signal 78 to the beam detection processing/control unit 66. Responsively, the beam detection processing/control unit 66 outputs a monitor switching signal 79 to the selector 70 and controls the selector 70 such that the irradiation device 3A (or the treatment room 7A) is selected as a connection destination. Upon completion of the switching operation, the selector 70 outputs an answer back signal 69 to the beam detection processing/control unit 66. Based on the answer back signal 69, the beam detection processing/control unit 66 determines whether the switching operation of the selector 70 has been normally completed (as described later in detail). If the normal switching operation is determined, the beam detection processing/control unit 66 outputs a switching end signal 80 to an AND circuit 81 in the central controller 55.

Also, when the switching end signal 76 and the power supply switching signal 75 from the AND circuit 73 are both inputted to the AND circuit 77 and the AND logical condition is satisfied, the AND circuit 77 outputs, in addition to the treatment room selection end signal 78, an accelerator preparation start signal 82 to the accelerator controller 13. Responsively, the accelerator controller 13 performs setting and preparation of the equipment constituting the charged particle beam generator 1, such as the pre-stage accelerator 11 and the synchrotron 12. Upon completion of the setting and preparation, the accelerator controller 13 outputs an accelerator preparation end signal 83 to the AND circuit 81 in the central controller 55.

The AND circuit 81 receives the accelerator preparation end signal 83 from the accelerator controller 13, the switching end signal 80 from the beam detection processing/control unit 66, the treatment room selection end signal 78 from the AND circuit 77, and a switching normal signal 68 (described later in detail) outputted when it is determined by a comparing and determining section 96 (see FIG. 5 described later) of the central controller 55 that the switching operation of the selector 70 has been normally completed. Then, when the AND logical condition is satisfied, the AND circuit 81 outputs an irradiation start preparation end signal 84 to an AND circuit 85 based on judgment that the irradiation start preparations for the treatment room 7A have been completed.

On the other hand, when the doctor (or the operator) in the treatment control room 40A operates an irradiation start button 46 on the console 49, an irradiation start signal 86 is outputted from the console 49 to the AND circuit 85 in the central controller 55.

When the irradiation start preparation end signal 84 from the AND circuit 81 and the irradiation start signal 86 from the console 49 are both inputted to the AND circuit 85 and the AND logical condition is satisfied, the AND circuit 85 outputs an irradiation start signal 87 to the accelerator controller 13 to start the irradiation. More specifically, the on/off switch (not shown) provided in the synchrotron 12 is closed by the accelerator controller 13, whereupon the supply of RF waves to the RF knockout electrode (not shown) is started and the extraction of the ion beam from the synchrotron 12 is also started.

During the beam irradiation, the information of the ion beam under irradiation is detected by the profile monitor 25, the energy monitor 29, the flatness monitor 30, and the dose monitor 31, which are mounted in the irradiation device 3A, and is inputted to the beam detection processing/control unit 66 through the selector 70. The beam detection processing/control unit 66 monitors the detected information. More specifically, it determines whether each item of the beam information detected by the profile monitor 25, the energy monitor 29 and the flatness monitor 30 is within a predetermined allowable range, and whether the dose detected by the dose monitor 31 has reached a predetermined dose. Further, the beam detection processing/control unit 66 outputs a beam information signal 88 to the display monitor 42 in the treatment control room 40A. As a result, the beam information during irradiation is displayed on the display monitor 42.

When the detected dose reaches the preset dose, the beam detection processing/control unit 66 outputs a dose attainment signal 89 to an OR circuit 90 in the central controller 55. On the other hand, when the doctor (or the operator) in the treatment control room 40A operates an irradiation stop button 47 on the console 49, an irradiation stop signal 91 is outputted from the console 49 to the OR circuit 90 in the central controller 55.

When either one of the irradiation stop signal 91 from the console 49 and the dose attainment signal 89 from the beam detection processing/control unit 66 is inputted to the OR circuit 90, the OR circuit 90 outputs an irradiation end signal 92 to the accelerator controller 13 to stop the irradiation. More specifically, the on/off switch (not shown) provided in the synchrotron 12 is opened by the accelerator controller 13, whereupon the supply of RF waves to the RF knockout electrode (not shown) is stopped and the extraction of the ion beam from the synchrotron 12 is also stopped.

When, during the irradiation, the beam detection processing/control unit 66 determines that any item of the beam information has exceeded the allowable range, the beam detection processing/control unit 66 outputs an abnormality signal 93 to an OR circuit 94 in the central interlock device 57. Responsively, the central interlock device 57 outputs an irradiation stop signal 95 to the accelerator controller 13, whereupon the extraction of the ion beam from the synchrotron 12 is stopped under control of the accelerator controller 13.

Although the sequence for selecting the treatment room is omitted in the above description, the central controller 55 may be designed, for example, to have the function of selecting one of the treatment rooms from which the beam request signal 74 issued from the console 49 in the corresponding treatment room 40A, 40B has been inputted at the earliest timing in the state where the positioning of the treatment room has been completed.

Figure 4:
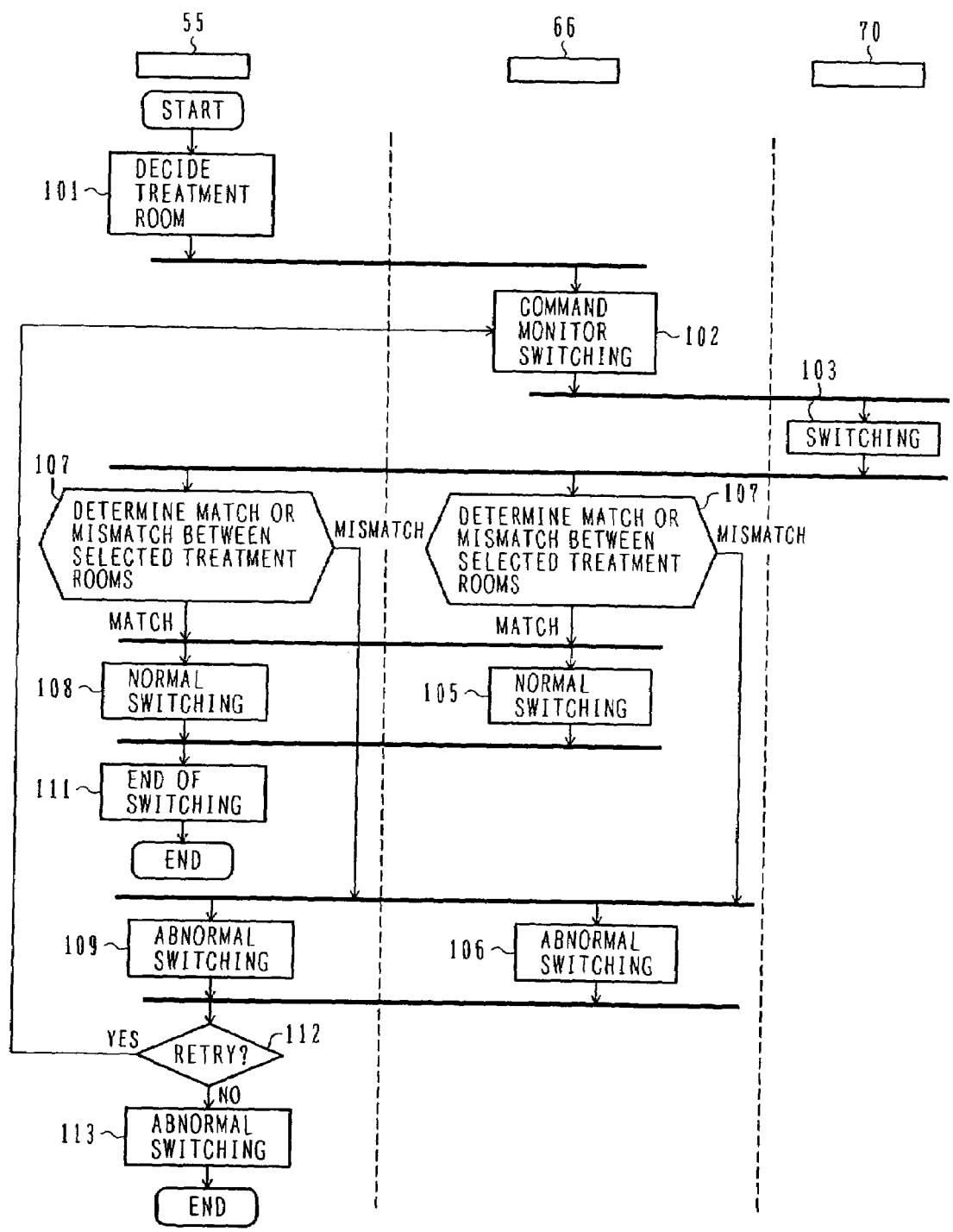
FIG. 4 is a flowchart of the functions executed by a central controller and a beam detection processing/control unit for determining whether the switching operation of a selector is normally completed.

While a description is omitted above for the sake of simplicity, each of the central controller 55 and the beam detection processing/control unit 66 in the therapy system of this embodiment has the function of determining whether the switching operation of the selector 70 has been normally completed. Unless it is determined by both the central controller 55 and the beam detection processing/control unit 66 that the switching operation of the selector 70 has been normally completed, the irradiation start preparation end signal 84 is never outputted from the AND circuit 81 to the AND circuit 85. FIG. 4 shows a flow of that determining function. In FIG. 4, the sequence of processing executed by the units (i.e., the central controller 55, the beam detection processing/control unit 66, and the selector 70) is shown successively in the vertical direction starting from the top.

First, the treatment room selection end signal 78 is outputted from the central controller 55 (exactly speaking, the AND circuit 77) to the beam detection processing/control unit 66 (step 101). In response to the treatment room selection end signal 78 thus inputted, the beam detection processing/control unit 66 outputs the monitor switching signal 79 to the selector 70 (step 102). The target to be monitored by the beam detection processing/control unit 66 is switched over in response to the monitor switching signal 79 inputted to the selector 70 (step 103).

Upon completion of the switching operation, the selector 70 outputs the answer back signal 69 to the beam detection processing/control unit 66. The beam detection processing/control unit 66 compares the monitor switching signal 79, which has been outputted as a command value, with the answer back signal 69 inputted as a response value, and determines whether the switching operation has been normally completed (step 104). If the treatment rooms represented by those two signals are matched with each other, this is regarded as indicating that the switching operation has been normally completed (step 105). Only after thus determining that the switching operation has been normally completed, the beam detection processing/control unit 66 outputs the switching end signal 80, described above with reference to FIG. 3, to the AND circuit 81 in the central controller 55. Conversely, if the treatment rooms represented by the two signals are mismatched, this is regarded as indicating that the switching operation has not been normally completed (step 106).

Also, the answer back signal 69 from the selector 70 is outputted to the comparing and determining section 96 (see FIG. 5 described later) of the central controller 55 in addition to the beam detection processing/control unit 66. The comparing and determining section 96 compares the treatment room selection end signal 78, which has been outputted as a command value, with the answer back signal 69 inputted as a response value, and determines whether the switching operation has been normally completed (step 107). If the treatment rooms represented by those two signals are matched with each other, this is regarded as indicating that the switching operation has been normally completed (step 108), and the comparing and determining section 96 outputs the switching normal signal 68 to the AND circuit 81. Conversely, if the treatment rooms represented by the two signals are mismatched, this is regarded as indicating that the switching operation has not been normally completed (step 109).

In such a way, if it is determined by both the beam detection processing/control unit 66 and the central controller 55 that the switching operation has been normally completed, final determination is made on the normal completion of the switching operation (step 111). In response to the final determination, as described above with reference to FIG. 3, the irradiation start preparation end signal 84 is outputted from the AND circuit 81 to the AND circuit 85 in the central controller 55 to progress the preparations for start of the irradiation. On the other hand, if the abnormal switching is determined by at least one of the beam detection processing/control unit 66 and the central controller 55, this is regarded as indicating that the switching operation of the selector 70 has not been normally completed, and whether to retry the switching operation or not is selected by the beam detection processing/control unit 66 (step 112). If the switching operation is not retried, the irradiation start preparation end signal 84 is not outputted from the AND circuit 81 to the AND circuit 85, and therefore the irradiation in the selected treatment room is disabled (step 113).

Incidentally, the above-described monitoring of the switching state of the selector 70 by the central controller 55 and the beam detection processing/control unit 66 is performed at all times even during the beam irradiation. Should the abnormal switching is determined during the irradiation, the central controller 55 outputs the abnormality signal to the central interlock device 57, thereby stopping the extraction of the ion beam from the synchrotron 12 through the accelerator controller 13.

Figure 5:
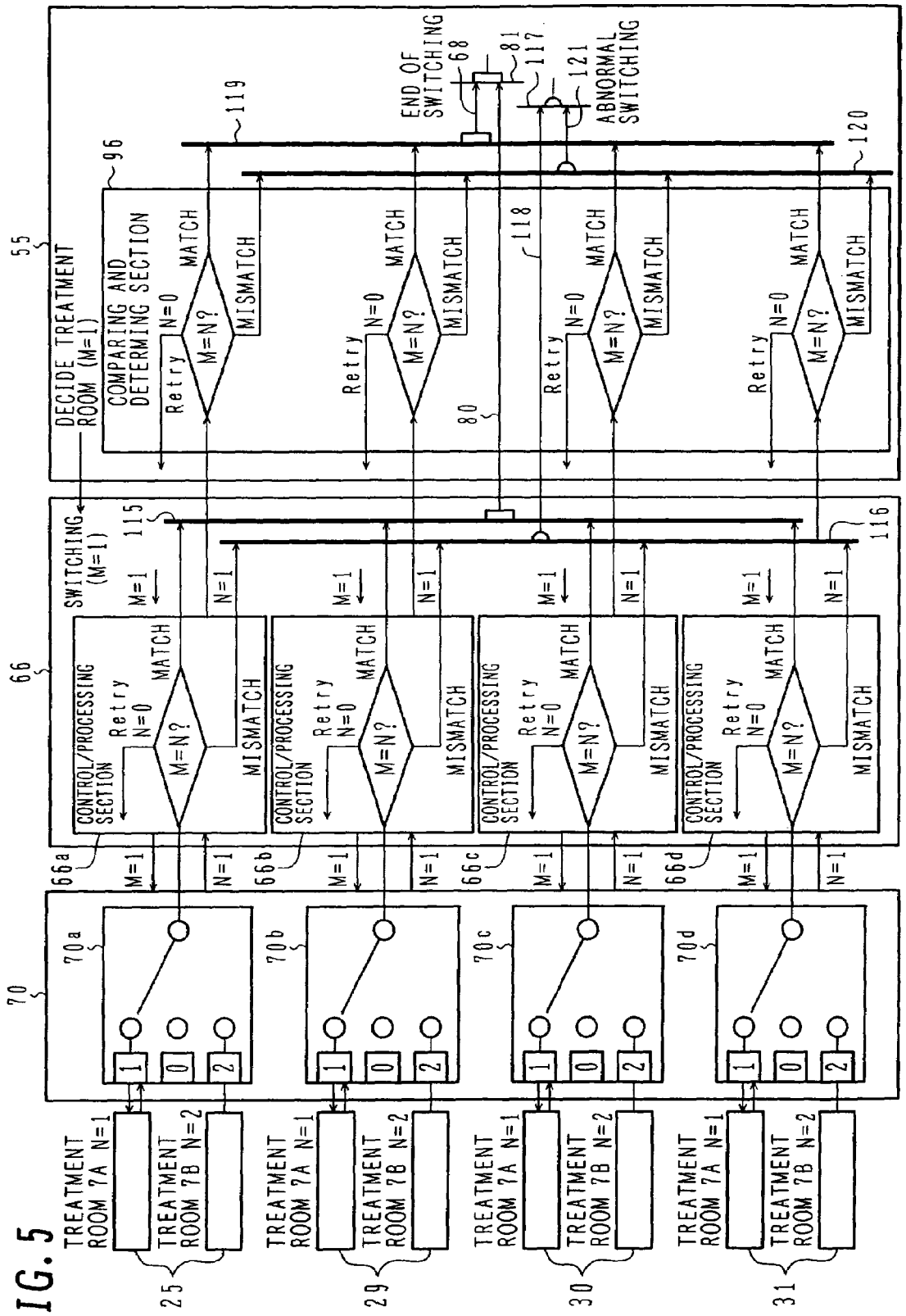
FIG. 5 is a chart showing the functions executed by the central controller and the beam detection processing/control unit for determining whether the switching operation of the selector is normally completed.

FIG. 5 shows, in more detail, the above-described switching determining function executed by the central controller 55 and the beam detection processing/control unit 66.

As shown in FIG. 5, the switching circuits 70a to 70d included in the selector 70 are each usually held in a position 0 corresponding to a state where neither the treatment room 7A nor the treatment room 7B are selected. When each switching circuit is switched over to a position 1, the corresponding detectors in the treatment room 7A (or the irradiation device 3A) are selected, and when it is switched over to a position 2, the corresponding detectors in the treatment room 7B (or the irradiation device 3B) are selected.

The central controller 55 outputs a command value M (corresponding to the above-mentioned treatment room selection signal 78) to the beam detection processing/control unit 66. The command value M is inputted to each of the control/processing sections 66a to 66d of the beam detection processing/control unit 66. Herein, M=1 represents the selection of the treatment room 7A, and M=2 represents the selection of the treatment room 7B. The control/processing sections 66a to 66d of the beam detection processing/control unit 66, to which the command value M has been inputted, apply the command value M to the switching circuits 70a to 70d of the selector 70, thereby performing the switching operations.

Selection values N from the detectors 25, 29, 30 and 31 on the side of the selected treatment room (i.e., the treatment room 7A in FIG. 5) are inputted to the switching circuits 70a to 70d of the selector 70, respectively. The switching circuits 70a to 70d output the selection values N (each corresponding to the above-mentioned answer back signal 69) to not only the control/processing sections 66a to 66d of the beam detection processing/control unit 66, but also to the comparing and determining section 96 of the central controller 55. Each of the control/processing sections 66a to 66d of the beam detection processing/control unit 66 compares the command value M with the selection value N and determines a match between M and N. Also, the comparing and determining section 96 of the central controller 55 compares the selection values N inputted from the switching circuits 70a to 70d with the corresponding command values M and determines a match between M and N.

If the control/processing sections 66a to 66d of the beam detection processing/control unit 66 determines a match between M and N, respective match signals are outputted to an AND circuit 115. When the match signals are inputted from all the control/processing sections 66a to 66d to the AND circuit 115 and the AND logical condition is satisfied, the AND circuit 115 outputs the above-mentioned switching end signal 80 to an AND circuit 81 in the central controller 55. On the other hand, if any of the control/processing sections 66a to 66d determines a mismatch between M and N, a mismatch signal 118 is outputted from an OR circuit 116 to an OR circuit 117 in the central controller 55.

Further, if the comparing and determining section 96 of the central controller 55 determines a match between the command value M and the selection value N inputted from corresponding one of the switching circuits 70a to 70d, a match signal is outputted to an AND circuit 119. When the match signals corresponding to all the switching circuits 70a to 70d are inputted to the AND circuit 119 and the AND logical condition is satisfied, the AND circuit 119 outputs the above-mentioned switching normal signal 68 to the AND circuit 81. On the other hand, if it is determined that any of the selection values N inputted from the switching circuits 70a to 70d is mismatched with the corresponding command value M, a mismatch signal 121 is outputted from an OR circuit 120 to the OR circuit 117.

When the switching normal signal 68 from the AND circuit 119 and the switching end signal 80 from the AND circuit 115 are both inputted to the AND circuit 81 and the AND logical condition is satisfied, this is regarded as indicating that the switching operation has been normally completed, and the AND circuit 81 outputs the irradiation start preparation end signal 84 to the AND circuit 85 to progress the preparations for start of the irradiation, as described above. On the other hand, if the mismatch signal 118 from the OR circuit 116 or the mismatch signal 121 from the OR circuit 120 is inputted to the OR circuit 117, this is regarded as indicating a switching abnormality, and the irradiation in the treatment room 7A is disabled.

If any of the control/processing sections 66a to 66d of the beam detection processing/control unit 66 and the comparing and determining section 96 of the central controller 55 determines that the corresponding selection value N is 0, this is regarded as indicating that the system is under switching or the switching operation is not properly performed, and the switching operation is repeated.

With the particle beam therapy system 100 of this embodiment, the system configuration of the control system 110 can be simplified. This point will be described below with reference to Comparative Example 1.

Figure 6:
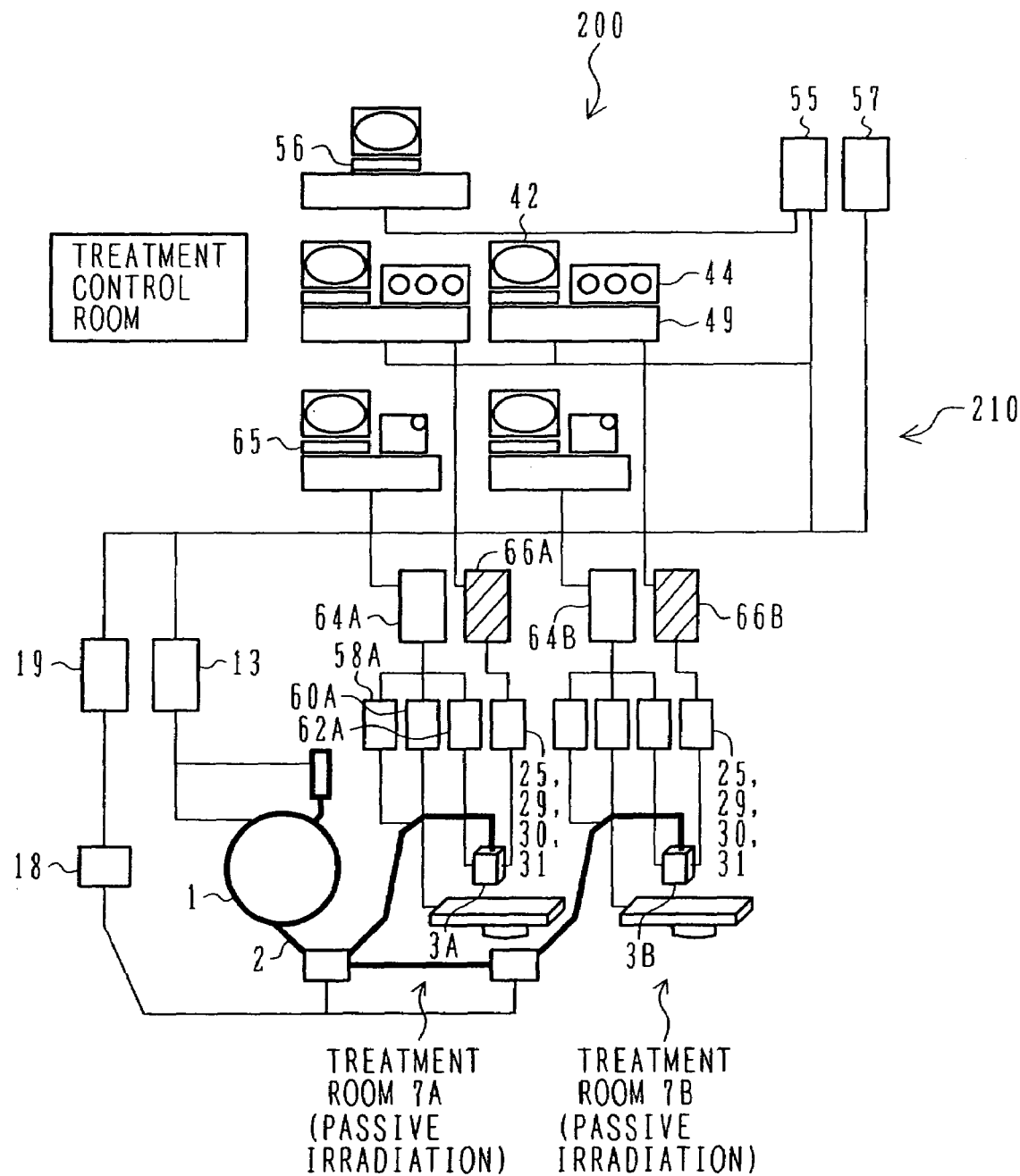
FIG. 6 is an overall block diagram of a particle beam therapy system of Comparative Example 1 in which a control system includes a beam detection processing/control unit in each treatment room.

FIG. 6 is an overall block diagram of a particle beam therapy system 200 of Comparative Example 1. This therapy system 200 differs from the therapy system 100 of the first embodiment in that a control system 210 for the former includes beam detection processing/control units 66A, 66B (indicated by hatched areas) provided in one-to-one relation to the treatment rooms 7A, 7B (or the irradiation devices 3A, 3B), and that the selector 70 is not provided in the former. The remaining configuration is the same as that of the control system 100.

In the therapy system having a plurality of treatment rooms to which Comparative Example 1 and this embodiment are applied, as described above, the ion beam extracted from the charged particle beam generator 1 is irradiated in only one treatment room and is never irradiated in a plurality of treatment rooms at the same time. Therefore, the beam detection processing/control units 66A, 66B provided in one-to-one relation to the treatment rooms 7A, 7B in the therapy system 200 of Comparative Example 1 are not necessarily required to be installed in the respective treatment rooms 7A, 7B because they serve to monitor the beam state during irradiation and are not used in the other treatment rooms than that under irradiation. Also, the beam detection processing/control units 66A, 66B do not take part in the positioning of the patient 20 and the setting of the irradiation field forming equipment, which are performed during the irradiation in the other selected treatment room. Accordingly, sharing the beam detection processing/control units 66A, 66B by the treatment rooms 7A, 7B will not lead to a reduction in the operation efficiency of the therapy system. Thus, the therapy system 200 of Comparative Example 1 is still susceptible to simplification in the configuration of the control system.

Figure 7:
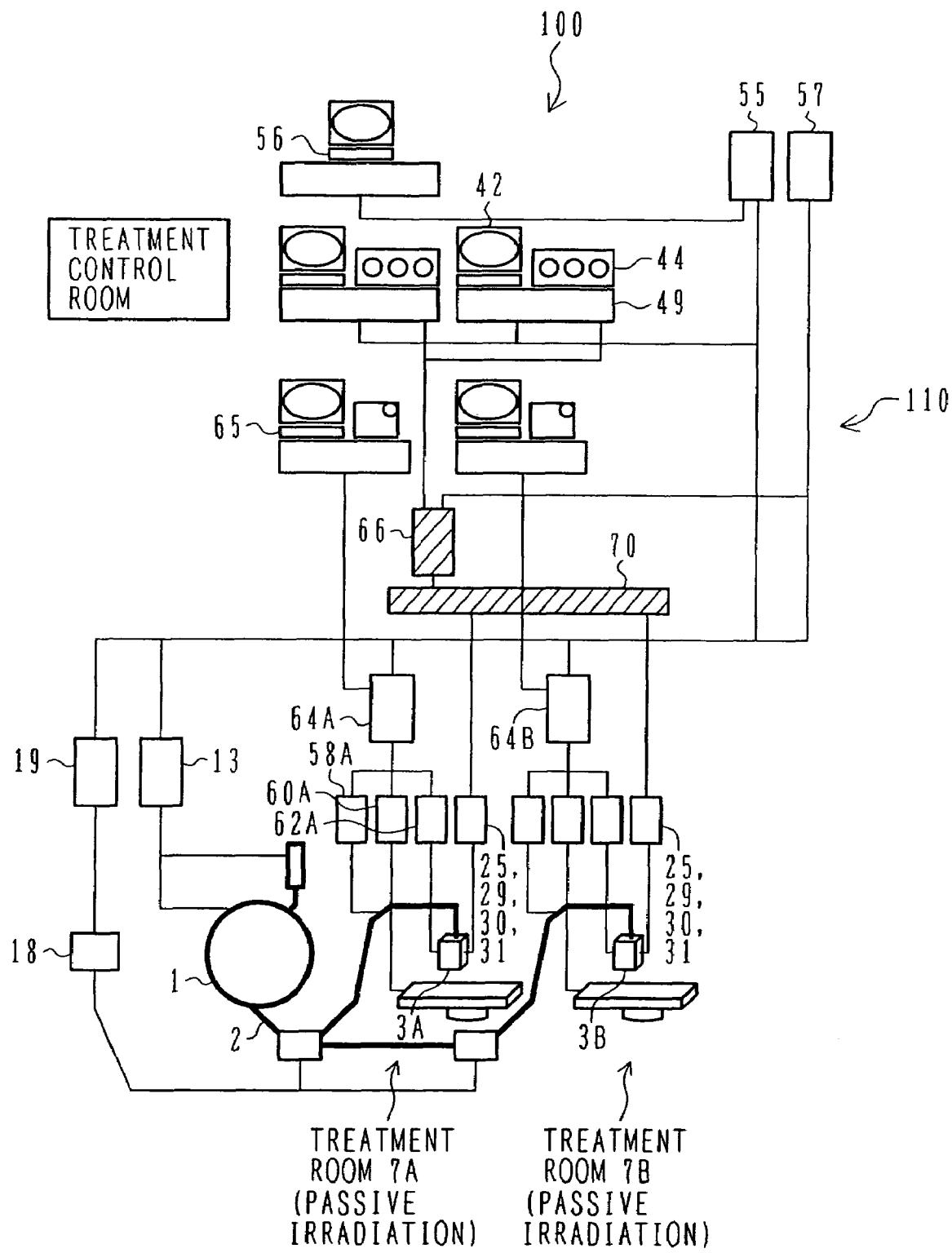
FIG. 7 is an overall block diagram of the particle beam therapy system according to the first embodiment of the present invention.

In contrast, with the control system 110 for the therapy system 100 of this embodiment, the beam detection processing/control unit 66 is shared by the treatment rooms 7A, 7B, as shown in FIG. 7, by providing the selector 70 to be able to switch over the irradiation device monitored by the beam detection processing/control unit 66 from one to the other, and by controlling the selector 70 such that the selector selectively establishes connection with the irradiation device in the treatment room to which the ion beam is to be transported through the beam line 2. Such a configuration means that the two beam detection processing/control units 66A, 66B indicated by hatched areas in FIG. 6 are replaced with the one beam detection processing/control unit 66 and the simple selector 70, which are indicated by hatched areas in FIG. 7. Therefore, the system configuration can be simplified as compared with the control system 210 of Comparative Example 1. In addition, the beam detection processing/control unit 66 does not take part in the positioning of the patient 20 and the setting of the irradiation field forming equipment, which are performed during in the treatment room not under irradiation, i.e., during the irradiation in the other selected treatment room. The gantry controllers 58A, 58B, the bed controllers 60A, 60B, the irradiation nozzle controllers 62A, 62B, and the irradiation controllers 64A, 64B, which are necessary for performing the preparations to start the irradiation, are installed in each of the treatment rooms. Accordingly, the operation efficiency of the therapy system is not reduced.

Further, with the particle beam therapy system 100 of this embodiment, system extensibility can be improved. More specifically, when adding a new treatment room, for example, a new beam detection processing/control unit must be installed in the case of the therapy system 200 of Comparative Example 1 described above with reference to FIG. 6. On the other hand, the therapy system 100 of this embodiment is adaptable for such an extension just by connecting a newly installed irradiation device to the selector 70 and adding a corresponding switching function to the selector 70. It is therefore possible to easily add a new treatment room and to improve the system extensibility.

While the above description has been made, by way example, in connection with the therapy system having two treatment rooms, the present invention is of course also applicable to a therapy system having three or more treatment rooms. The above-mentioned effects of the therapy system of this embodiment in simplifying the system configuration and improving the system extensibility become more noticeable as the number of treatment rooms increases.

Second Embodiment

Figure 8:
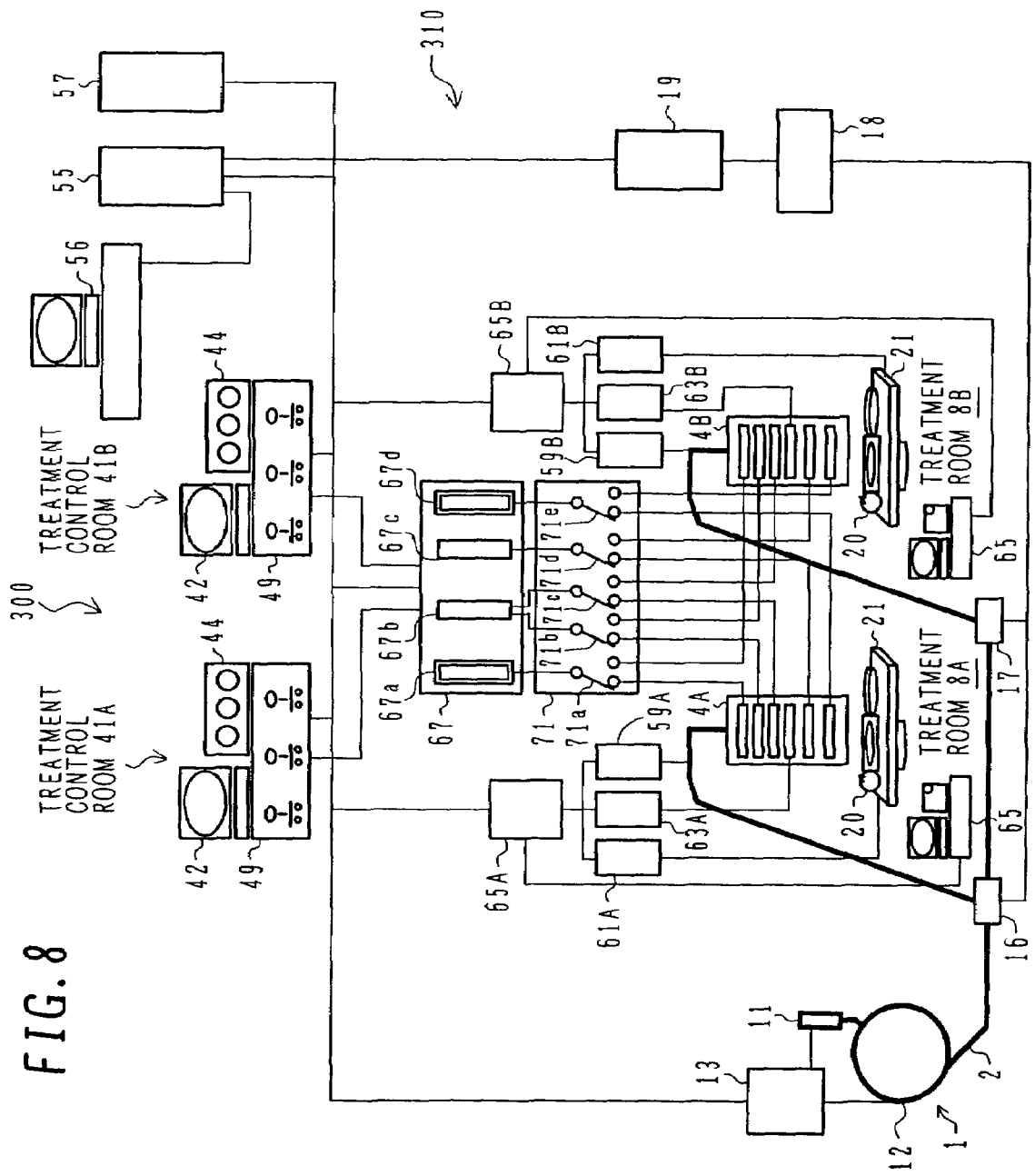
FIG. 8 is an overall block diagram of a particle beam therapy system according to a second embodiment of the present invention.

A charged particle therapy system according to another preferred embodiment of the present invention will be described below as a second embodiment with reference to FIG. 8. In contrast with the first embodiment in which the present invention is applied to the therapy system 100 having a plurality of treatment rooms for passive irradiation, the present invention is applied to a therapy system having a plurality of treatment rooms for scanning irradiation in this second embodiment.

Figure 9:
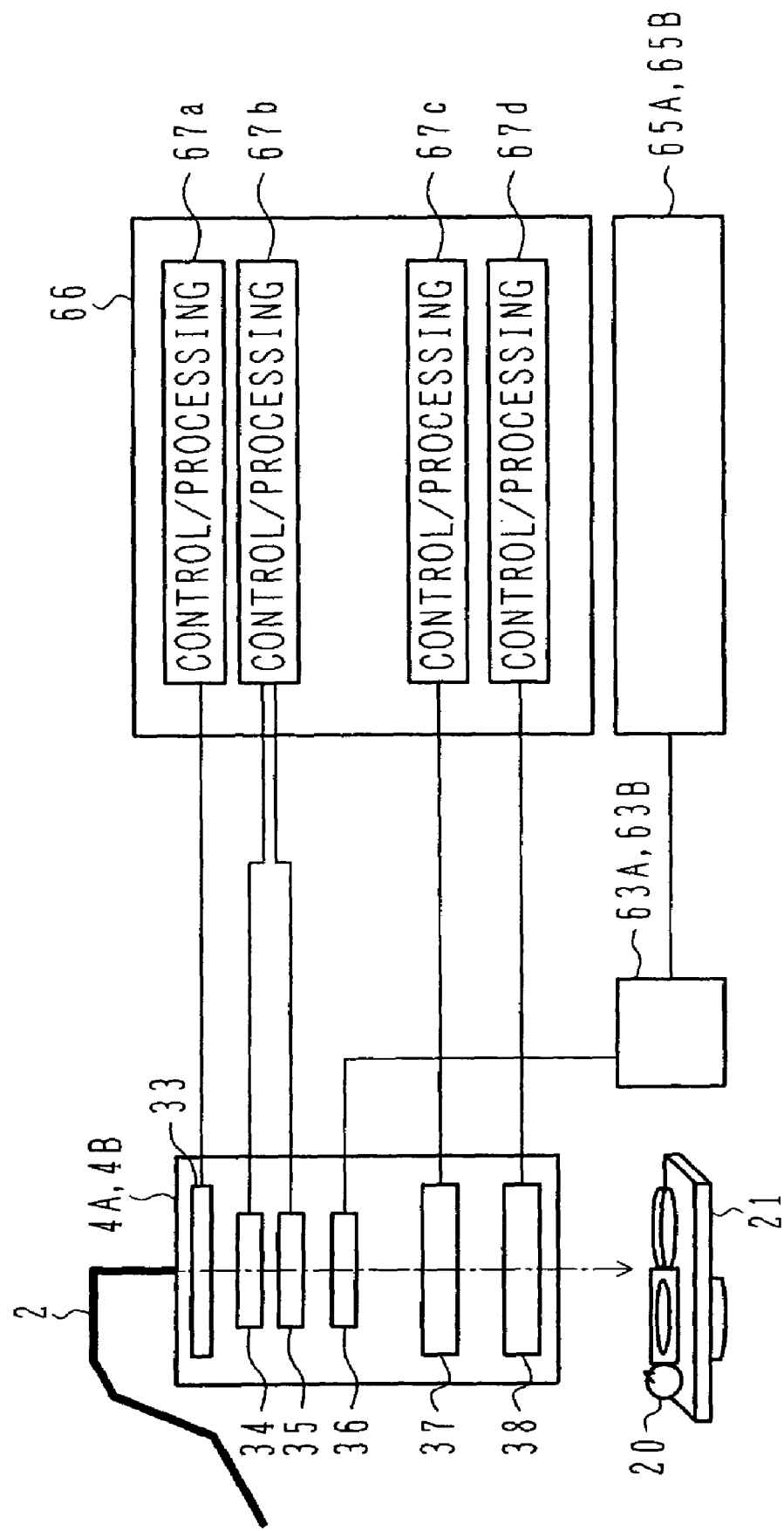
FIG. 9 is a schematic view showing a general equipment configuration of an irradiation device with scanning irradiation shown in FIG. 8.

A charged particle therapy system 300 of this embodiment includes treatment rooms 8A, 8B in which are installed respectively irradiation devices 4A, 4B of the scanning irradiation type scanning a fine beam and irradiating the scanned beam to the affected part in the body of the patient 20. FIG. 9 schematically shows a general equipment configuration of each of the irradiation devices 4A, 4B.

As shown in FIG. 9, each of the scanning irradiation devices 4A, 4B includes a profile monitor (detector) 33 for measuring the centroid and width of the ion beam entering the irradiation device 4A, 4B from the beam line 2, scanning magnets 34, 35 for bending the ion beam to a position suitable for irradiation to a target, a scatterer 36 for deciding the width of the irradiation beam, a spot position monitor (detector) 37 for measuring the centroid and width of the ion beam bent by the scanning magnets 34, 35, and a dose monitor (detector) 38 for detecting the dose. Those units 33 to 38 are mounted in the irradiation device in the mentioned order from the upstream side in the direction of travel of the beam.

A control system 310 for the therapy system 300 of this embodiment includes a beam detection processing/control unit (monitoring unit, first control unit, determining unit, and scan stroke control unit) 67 for both the treatment rooms 8A, 8B. The functions of the beam detection processing/control unit 67 will be described below.

As shown in FIG. 9, of the equipment mounted in each scanning irradiation device 4A, 4B, the scatterer 36 for forming the irradiation field is controlled by the above-mentioned irradiation nozzle controller 63A, 63B. Because the scatterer 36 is mounted in match with the irradiation target, the irradiation nozzle controller 63A, 63B makes monitoring to avoid a possibility that a false scatterer is mounted.

On the other hand, beam information obtained from those detectors among the equipment mounted in the irradiation device 4A, 4B which are used to detect the beam information of the ion beam under irradiation, i.e., the profile monitor 33, the spot position monitor 37, and the dose monitor 38, is taken into the beam detection processing/control unit 67. The beam detection processing/control unit 67 has not only the function of determining whether each item of the beam information detected by those detectors is within a predetermined allowable range, but also the function of controlling the scanning magnets 34, 35. More specifically, the beam detection processing/control unit 67 includes a control/processing section 67a for taking in the information measured by the profile monitor 33, computing the centroid and width of the ion beam, and detecting an abnormality of the centroid or width when the computed result exceeds an allowable value, a control/processing section 67b for comparing preset current values of the scanning magnets 34, 35 with actually measured current values and controlling the scanning magnets 34, 35 in accordance with the compared results, a control/processing section 67c for computing the centroid and width of the scanned ion beam from the information measured by the spot position monitor 37 and detecting an abnormality of the ion beam when the computed results exceed respective allowable values, and a control/processing section 67d for monitoring the dose from the information measured by the dose monitor 38 and detecting attainment of the target dose when the monitored does has reached a preset value. When the beam abnormality or the dose attainment is detected by the beam detection processing/control unit 67, the extraction of the ion beam from the synchrotron 12 is stopped in the same way as that in the beam detection processing/control unit 66 described above.

Returning to FIG. 8, the control system 310 includes one beam detection processing/control unit 67 for the two irradiation devices 4A, 4B, and one of those two irradiation devices, which is to be monitored by the beam detection processing/control unit 67, is selected by a selector 71. In other words, the beam detection processing/control unit 67 is shared by the irradiation devices 4A, 4B (or the treatment rooms 8A, 8B).

The selector 71 includes a switching circuit 71a for switching over the profile monitors 33, 33 of the irradiation devices 4A, 4B, a switching circuit 71b for switching over the scanning magnets 34, 34 of the irradiation devices 4A, 4B, a switching circuit 71c for switching over the scanning magnets 35, 35 of the irradiation devices 4A, 4B, a switching circuit 71d for switching over the spot position monitors 37, 37 of the irradiation devices 4A, 4B, and a switching circuit 71e for switching over the dose monitors 38, 38 of the irradiation devices 4A, 4B. Those switching circuits 71a to 71e are all always turned to the same side when switched over, without being irregularly turned to the different sides.

The remaining configuration of the therapy system 300 of this embodiment is the same as that in the foregoing therapy system 100.

With the therapy system 300 of this embodiment, as with the first embodiment described above, the system configuration can be simplified while maintaining the operation efficiency, and the system extensibility can be improved. In general, the scanning irradiation is required to handle a larger number of input signals from the detectors and therefore to use a more complicated beam detection processing/control unit than that used in the passive irradiation. For that reason, a greater effect can be obtained in the case of applying the present invention to a scanning irradiation therapy system like this embodiment than in the case of applying the present invention to a passive irradiation therapy system like the first embodiment.

Third Embodiment

Figure 10:
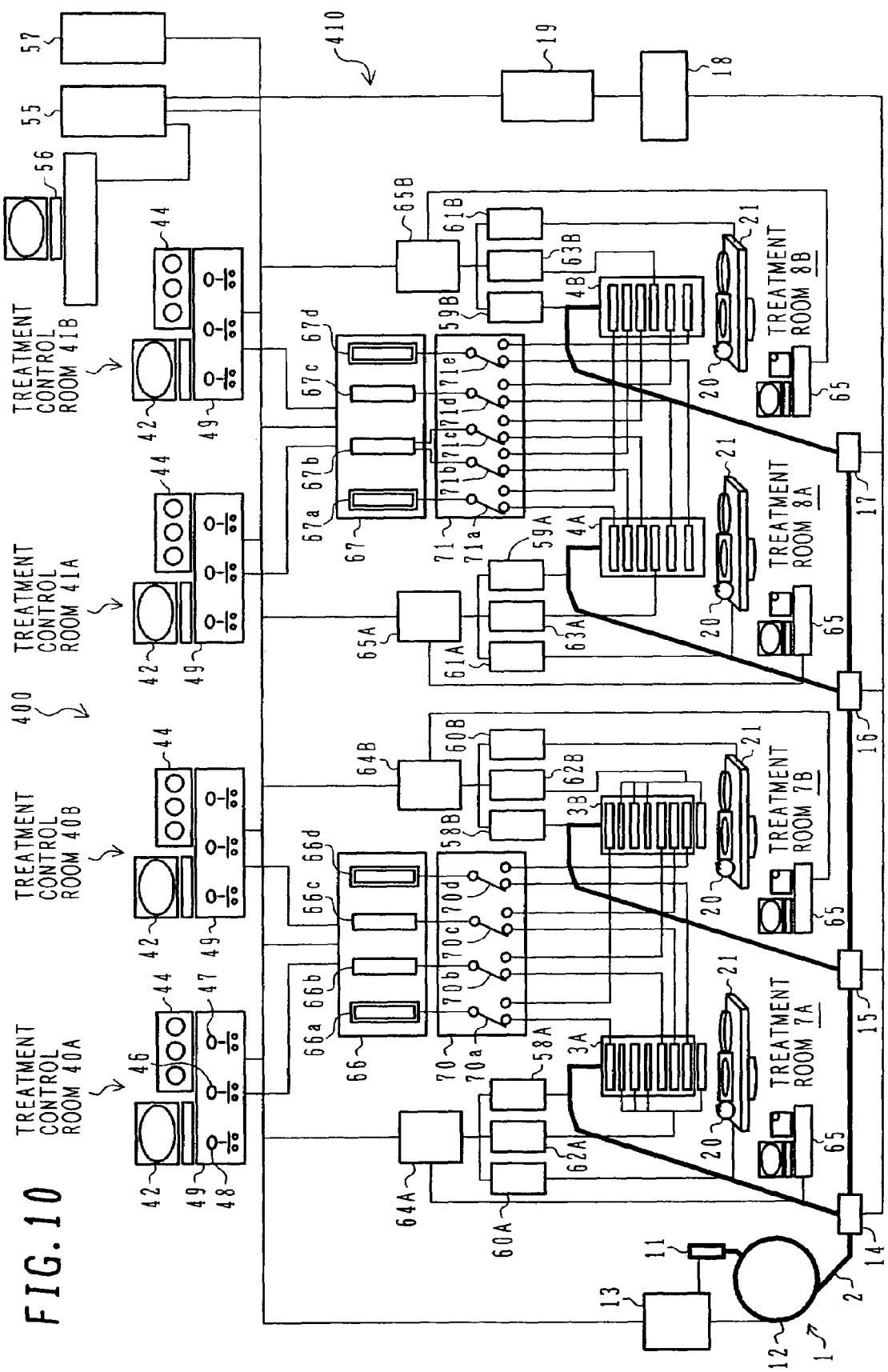
FIG. 10 is an overall block diagram of a particle beam therapy system according to a third embodiment of the present invention.

A charged particle therapy system according to still another preferred embodiment of the present invention will be described below as a third embodiment with reference to FIG. 10. In contrast with the first and second embodiments in which the present invention is applied to the therapy system having a plurality of treatment rooms for the same irradiation method, the present invention is applied to a therapy system having a plurality of treatment rooms for the different irradiation methods in this third embodiment.

A charged particle therapy system 400 of this embodiment is a system including both the configuration of the therapy system 100 described above as the first embodiment and the configuration of the therapy system 300 described above as the second embodiment. More specifically, the charged particle therapy system 400 has four treatment rooms, i.e., treatment rooms 7A, 7B equipped with irradiation devices 3A, 3B of the passive irradiation type and treatment rooms 8A, 8B equipped with irradiation devices 4A, 4B of the scanning irradiation type. The equipment configuration of each of the irradiation devices 3A, 3B and the irradiation devices 4A, 4B is the same as that in the first and second embodiments.

An ion beam extracted from a synchrotron 12 in a charged particle beam generator 1 is transported to selected one of the treatment rooms 7A, 7B, 8A and 8B through a beam line 2. The beam line 2 includes switching magnets (bending magnets) 14 to 17. The ion beam introduced to the beam line 2 is selectively transported to one of the treatment rooms 7A, 7B, 8A and 8B depending on switching-over between excitation and non-excitation of the switching magnets 14 to 17 through a magnet power supply 18. The magnet power supply 18 is controlled by a power supply controller 19.

Treatment control rooms 40A, 40B, 41A and 41B where the operations necessary for the treatment, etc. are carried out are installed near the treatment rooms 7A, 7B, 8A and 8B, respectively. Each of the treatment control rooms 40A, 40B, 41A and 41B includes a display monitor 42, an operating/monitoring panel 44, and a console 49.

A control system 410 for the charged particle therapy system 400 comprises a central controller 55, a treatment planning system 56, a central interlock device 57, an accelerator controller 13, and the power supply controller 19. Furthermore, the control system 410 includes, in the treatment rooms 7A, 7B, 8A and 8B in one-to-one relation, gantry controllers 58A, 58B, 59A and 59B, bed controllers 60A, 60B, 61A and 61B, irradiation nozzle controllers 62A, 62B, 63A and 63B, and irradiation controllers 64A, 64B, 65A and 65B for controlling those corresponding three controllers in a supervisory manner. In addition, the control system 410 includes a beam detection processing/control unit 66 provided for the two treatment rooms 7A, 7B, and a beam detection processing/control unit 67 provided for the two treatment rooms 8A, 8B. The configurations and functions of the beam detection processing/control units 66, 67 are the same as those in the first and second embodiments. In other words, the beam detection processing/control units 66, 67 monitor beam information in the irradiation devices 3A, 3B, 4A and 4B. If a beam abnormality is detected, or if attainment of target dose is detected, the extraction of the ion beam from the synchrotron 12 is stopped, whereby excess irradiation and false irradiation to the patient 20 can be avoided.

The irradiation devices to be monitored by the beam detection processing/control units 66, 67 are selected by the selectors 70, 71, respectively. The configurations and functions of the selectors 70, 71 are the same as those in the first and second embodiments. The switching operations of the selectors 70, 71 are performed by the beam detection processing/control units 66, 67 (more exactly speaking, switching circuits 70a to 70d of the selector 70 are switched respectively by control/processing sections 66a to 66d of the beam detection processing/control unit 66, and switching circuits 71a to 71e of the selector 71 are switched respectively by control/processing sections 67a to 67d of the beam detection processing/control unit 67) so as to establish connection with the selected treatment room (i.e., the treatment room to which the ion beam is transported through the beam line 2). Whether the switching operation of the selector 70 has been normally completed is determined by both the central controller 55 (i.e., a comparing and determining section 96 therein) and the beam detection processing/control unit 66, and whether the switching operation of the selector 71 has been normally completed is determined by both the central controller 55 (i.e., the comparing and determining section 96 therein) and the beam detection processing/control unit 67. Unless the switching operation has been normally completed, the irradiation in the selected treatment room is stopped.

The remaining configuration of the therapy system 400 of this embodiment is the same as that of the therapy systems 100 and 300 described above.

With the particle beam therapy system 400 of this embodiment, the system configuration of the control system 410 can be simplified. This point will be described below with reference to Comparative Example 2.

Figure 11:
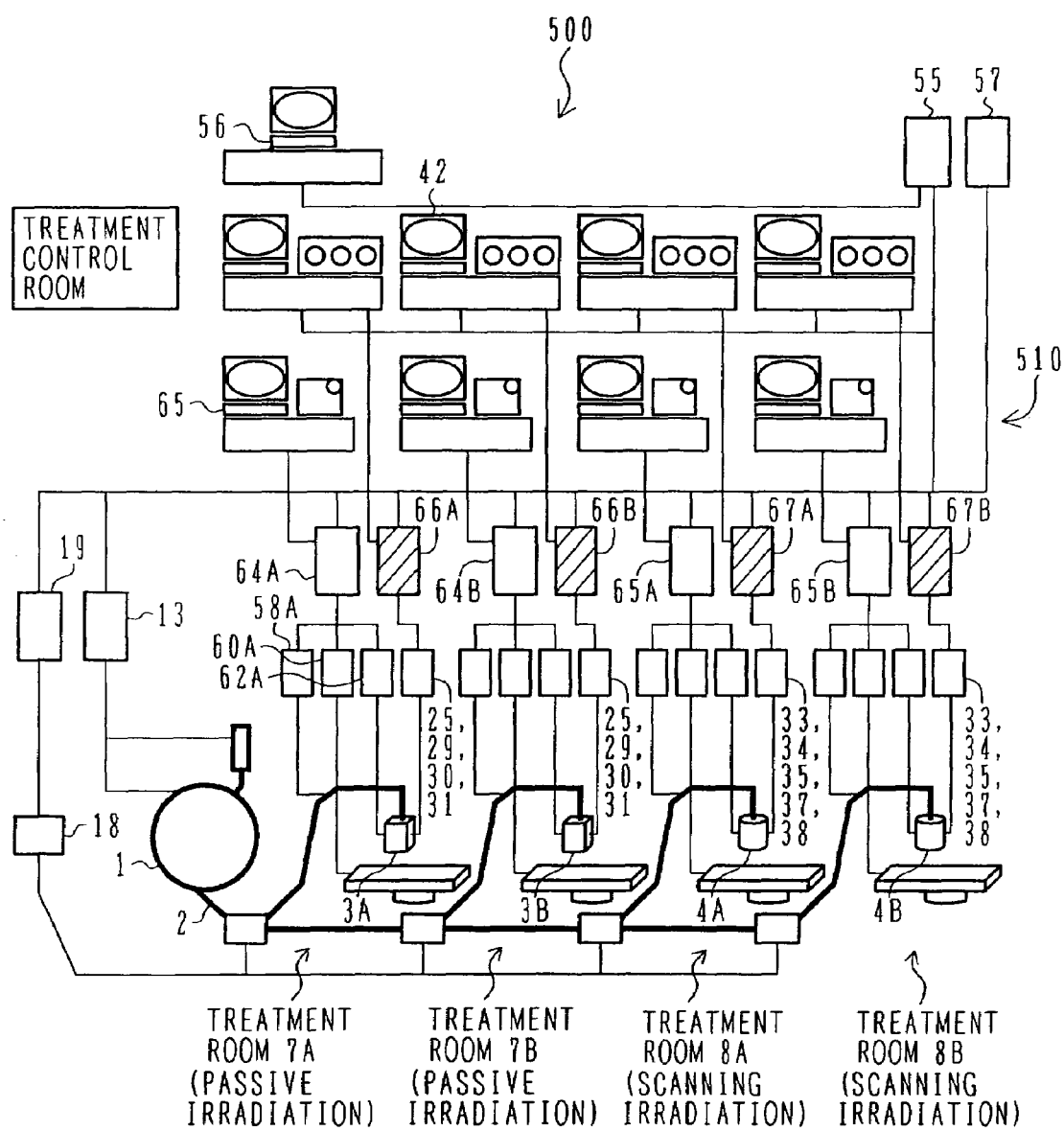
FIG. 11 is an overall block diagram of a particle beam therapy system of Comparative Example 2 in which a control system includes a beam detection processing/control unit in each treatment room.

FIG. 11 is an overall block diagram of a particle beam therapy system 500 of Comparative Example 2. This therapy system 500 differs from the therapy system 400 of the third embodiment in that a control system 510 for the former includes beam detection processing/control units 66A, 66B, 67A and 67B (indicated by hatched areas) provided in one-to-one relation to the treatment rooms 7A, 7B, 8A and 8B (or the irradiation devices 3A, 3B, 4A and 4B), and that the selectors 70, 71 are not provided in the former. The remaining configuration is the same as that of the therapy system 400.

Figure 12:
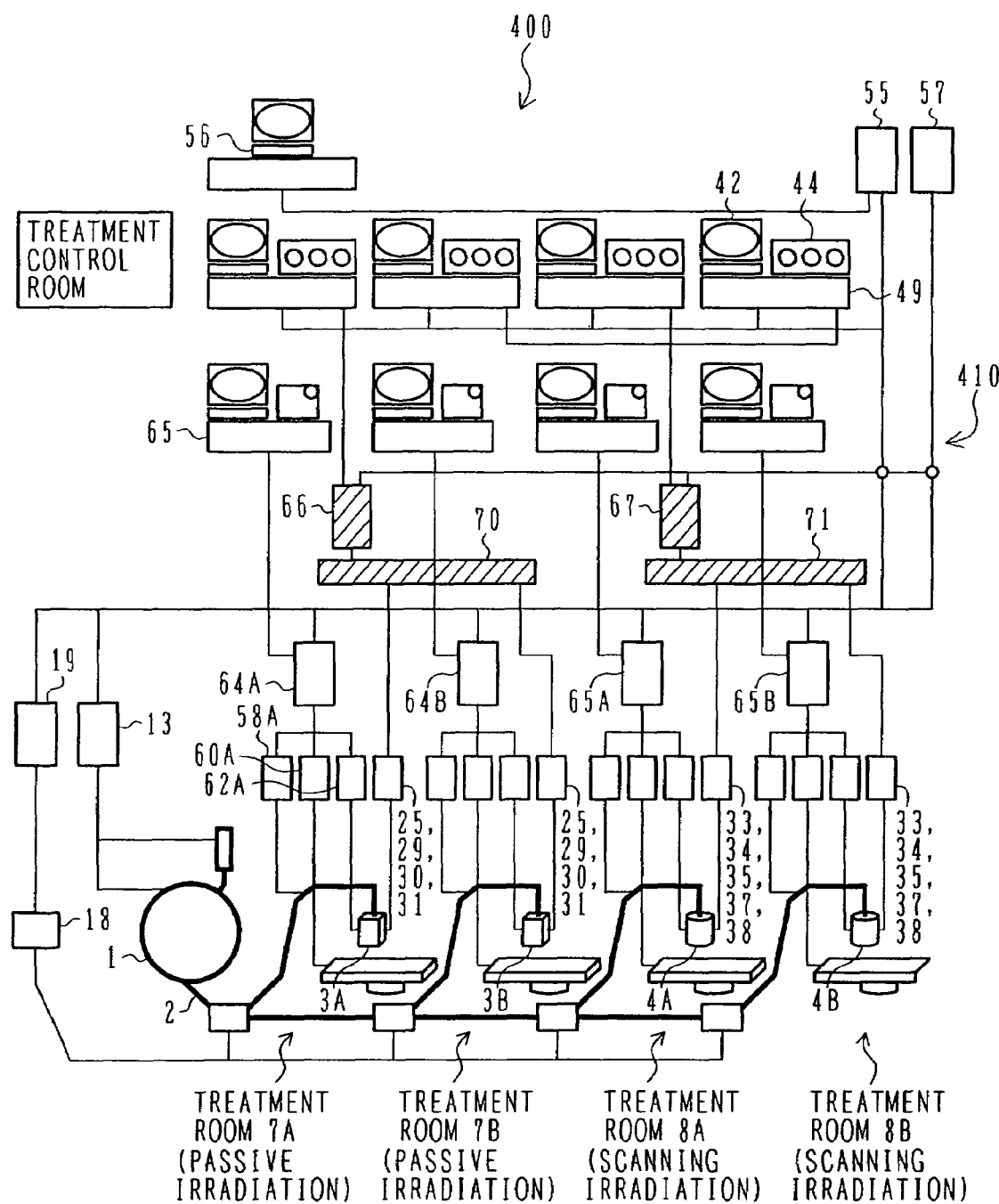
FIG. 12 is an overall block diagram of the particle beam therapy system according to the third embodiment of the present invention.

In contrast, with the control system 410 for the therapy system 400 of this embodiment, the beam detection processing/control unit 66 is shared by the treatment rooms 7A, 7B and the beam detection processing/control unit 67 is shared by the treatment rooms 8A, 8B, as shown in FIG. 12, by providing the selector 70 to be able to switch over the irradiation device monitored by the beam detection processing/control unit 66 from one to the other, providing the selector 71 to be able to switch over the irradiation device monitored by the beam detection processing/control unit 67 from one to the other, and by controlling the selectors 70, 71 such that the selector 70 or 71 selectively establishes connection with the irradiation device in the treatment room to which the ion beam is to be transported through the beam line 2. Such a configuration means that the four beam detection processing/control units 66A, 66B, 67A and 67B indicated by hatched areas in FIG. 11 are replaced with the two beam detection processing/control unit 66, 67 and the simple selectors 70, 71, which are indicated by hatched areas in FIG. 12. Therefore, the system configuration can be simplified as compared with the control system 510 of Comparative Example 2. In addition, the gantry controllers 58A, 58B, 59A and 59B, the bed controllers 60A, 60B, 61A and 61B, the irradiation nozzle controllers 62A, 62B, 63A and 63B, and the irradiation controllers 64A, 64B, 65A and 65B, which are necessary for performing the preparations to start the irradiation, are installed in each of the treatment rooms. Accordingly, the operation efficiency of the therapy system is not reduced.

Figure 13:
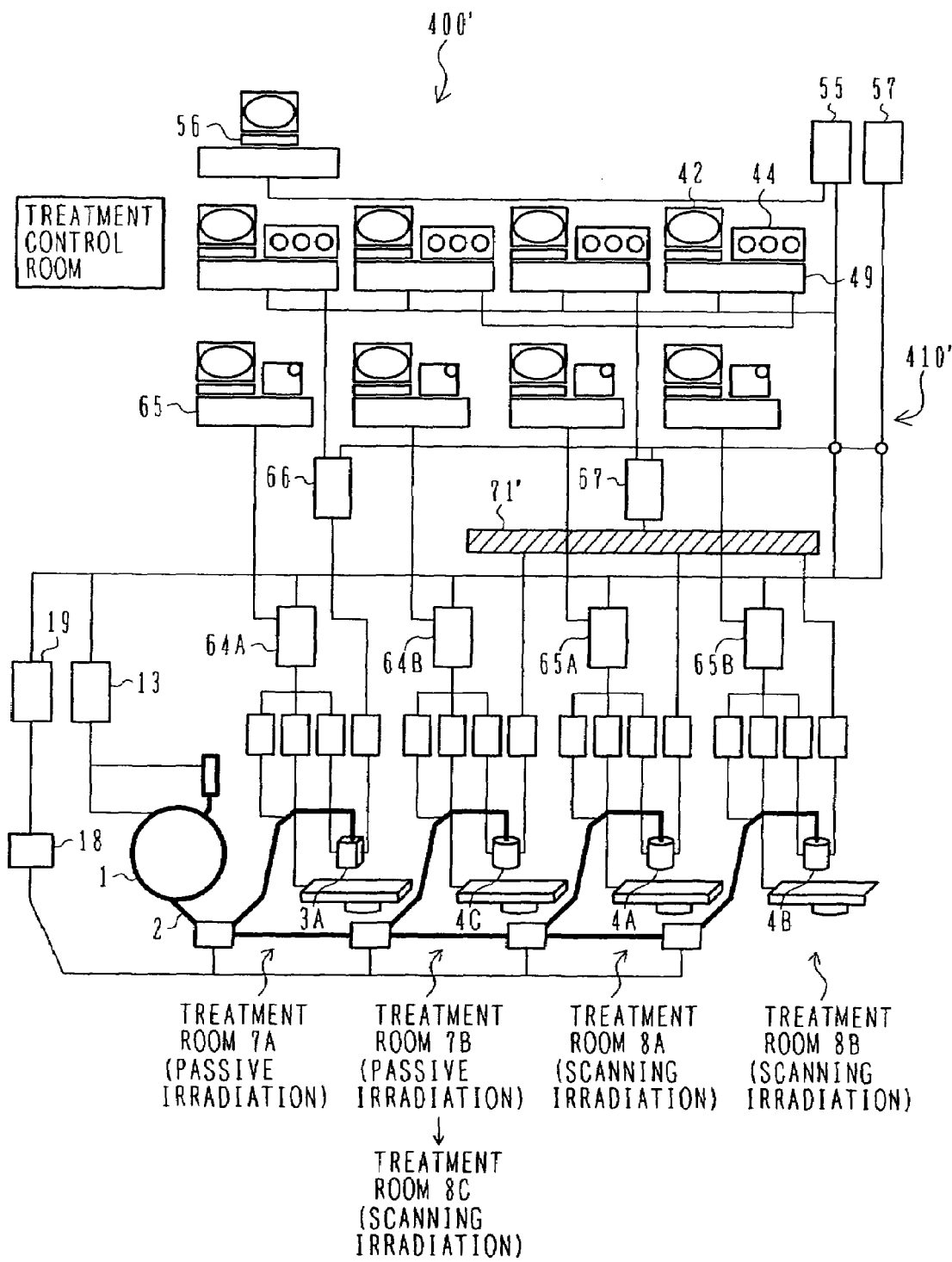
FIG. 13 shows a modification of the particle beam therapy system, shown in FIG. 12, in which one treatment room for passive irradiation is replaced with a treatment room for scanning irradiation.

Further, with the particle beam therapy system 400 of this embodiment, system flexibility and extensibility can be improved. This point will be described below with reference to FIG. 13. FIG. 13 is an overall block diagram of a particle beam therapy system 400' modified from the particle beam therapy system 400 of this embodiment such that the irradiation method for the treatment room 7B is changed from the passive irradiation to the scanning irradiation (namely, the irradiation device 3B of the passive radiation type is replaced with an irradiation device 4C of the scanning irradiation type).

In FIG. 13, the therapy system 400' has the treatment room 7A equipped with the passive irradiation device 3A and the treatment rooms 8A, 8B and 8C equipped with the scanning irradiation devices 4A, 4B and 4C, respectively. The treatment room 8C is a treatment room equipped with the irradiation device 4C prepared by changing the irradiation method in the treatment room 7B from passive irradiation to scanning irradiation. Detectors 33, 37 and 38 and scanning magnets 34, 35 all mounted in the irradiation device 4C are connected to a selector 71' (indicated by a hatched area in FIG. 13) which is modified to have a newly added switching function. On the other hand, since the switching operation on the side of the irradiation device 3A is no longer required, the detectors 25, 29, 30 and 31 mounted in the irradiation device 3A are connected to the beam detection processing/control unit 66 without interposing the selector 70 therebetween.

When changing the irradiation method for the treatment room 7B from passive irradiation to scanning irradiation like such a modification, in the therapy system 500 of Comparative Example 2 described above with reference to FIG. 11, the beam detection processing/control unit 66B adapted for the passive irradiation must be entirely replaced with a beam detection processing/control unit adapted for the scanning irradiation. In contrast, as shown in FIG. 13, the therapy system 400 of this embodiment is easily adaptable for such a modification just by reconnecting the new irradiation device 4C of the scanning irradiation type to the selector 71' added with a correspondingly added switching function. Another additional advantage is that the selector 70 for the passive irradiation side can be dispensed with. It is therefore possible to relatively easily change the irradiation method used in the treatment room and to improve the system flexibility.

Similarly, when adding a new treatment room, the therapy system 400 of this embodiment is adaptable for such an extension just by connecting an irradiation device installed in the new treatment room to the selector 70 when the installed irradiation device is of the passive irradiation type, and by connecting an irradiation device installed in the new treatment room to the selector 71 when the installed irradiation device is of the scanning irradiation type, followed by adding a corresponding switching function to the selector 70 or 71. It is therefore possible to easily add a new treatment room and to improve the system extensibility.

In general, the scanning irradiation is required to handle a larger number of input signals from the detectors and therefore to employ a more complicated beam detection processing/control unit than that in the passive irradiation. Accordingly, the above-mentioned effects in improving the system flexibility and extensibility become more noticeable particularly when the irradiation method is changed from passive irradiation to scanning irradiation, or when a new treatment room for the scanning irradiation is added.

Fourth Embodiment

A charged particle therapy system according to still another preferred embodiment of the present invention will be described below as a fourth embodiment. In contrast with the third embodiment in which the beam detection processing/control unit is shared by the treatment rooms utilizing the same irradiation method, this fourth embodiment is configured such that the beam detection processing/control unit is further shared by the treatment rooms utilizing the different irradiation methods.

Figure 14:
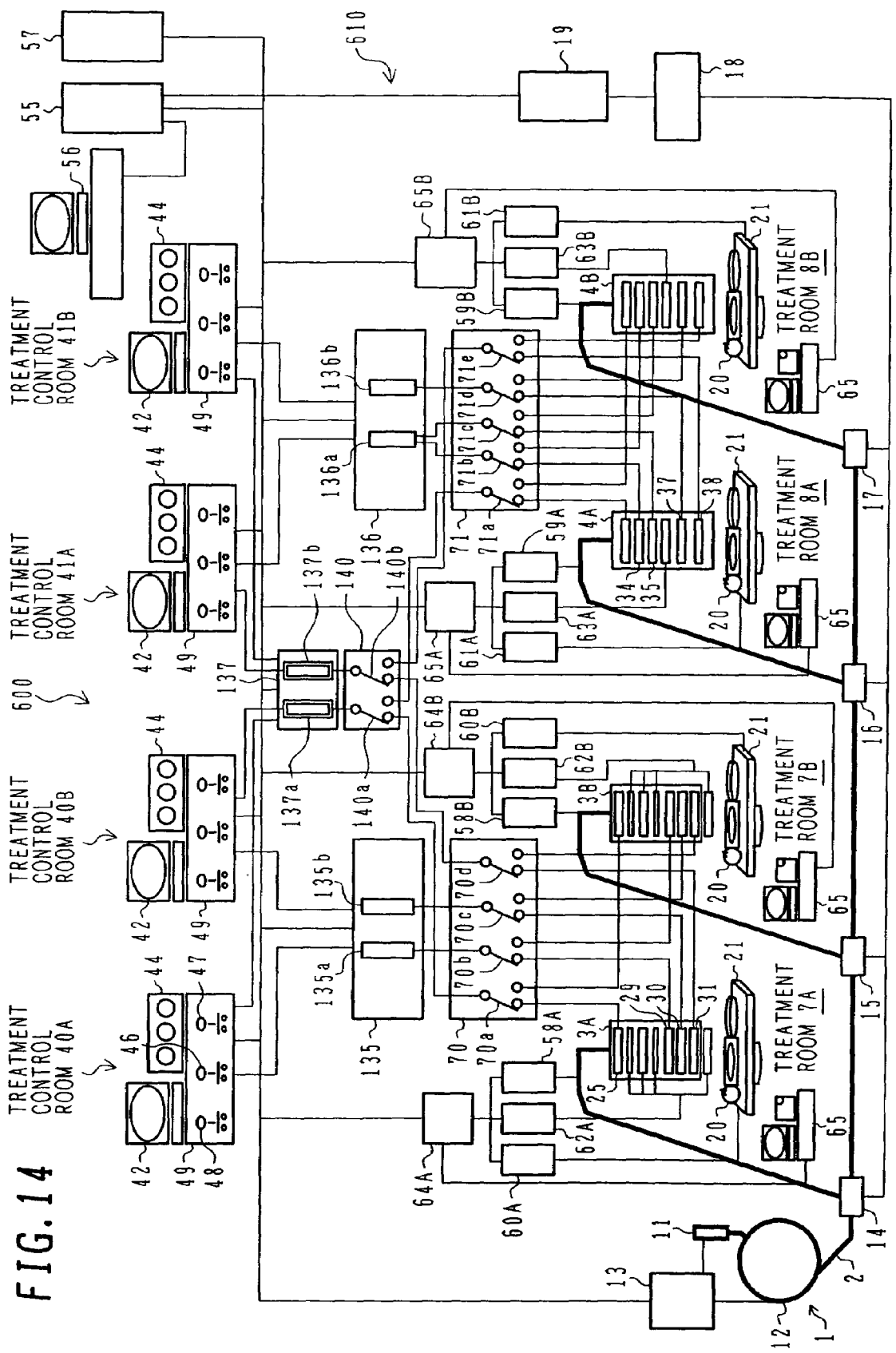
FIG. 14 is an overall block diagram of a particle beam therapy system according to a fourth embodiment of the present invention.

FIG. 14 is an overall block diagram of a particle beam therapy system 600 according to the fourth embodiment. As shown in FIG. 14, a beam detection processing/control unit (monitoring unit, first control unit, and determining unit) 135 shared on the passive irradiation side includes control/processing sections 135*a*, 135*b* for monitoring respectively the energy monitors 29 and the flatness monitors 30 among the detectors mounted in the passive irradiation devices 3A, 3B, while a beam detection processing/control unit (monitoring unit, first control unit, determining unit, and scan stroke control unit) 136 shared on the scanning irradiation side includes control/processing sections 136*a*, 136*b* for monitoring respectively the scanning magnets 34, 35 mounted in the scanning irradiation devices 4A, 4B and the spot position monitors 37 among the detectors mounted therein. Also, a beam detection processing/control unit (monitoring unit, first control unit, and determining unit) 137 shared on both the passive irradiation and the scanning irradiation sides includes control/processing sections 137*a*, 137*b* for monitoring respectively the profile monitors 25, 33 and the dose monitors 31, 38 among the detectors mounted in the passive and scanning irradiation devices 3A, 3B, 4A and 4B.

Although the constructions and functions of the selectors 70, 71 are the same as those in the first to third embodiments described above, the connection source side of the switching circuits 70*a*, 70*d*, 71*a* and 71*e* is connected to a selector 140 instead of the beam detection processing/control units. The selector 140 serves as a unit for switching over a target, which is monitored by the beam detection processing/control unit 137 to obtain the beam information, between the passive irradiation side (i.e., the side of the passive irradiation devices 3A, 3B) and the scanning irradiation side (i.e., the side of the scanning irradiation devices 4A, 4B). Then, the selector 140 has a switching circuit 140*a* for switching over the profile monitors 25, 33 and a switching circuit 140*b* for switching over the dose monitors 31, 38. In other words, the switching-over between the profile monitors 25, 33 and the switching-over between the dose monitors 31, 38 are each performed in two stages by the selector 140 and the selector 70 or 71.

The remaining configuration is the same as that in the above-described third embodiment, and hence a description thereof is omitted here.

Thus, with attention paid to the fact that some detectors, i.e., the profile monitor and the dose monitor, are in common between the irradiation devices utilizing the different irradiation methods, i.e., between the passive irradiation devices 3A, 3B and the scanning irradiation devices 4A, 4B, the therapy system of this embodiment is designed so as to share the beam detection processing/control unit 137 by the treatment rooms utilizing the different irradiation methods, in addition to sharing each of the beam detection processing/control units 135, 136 by the treatment rooms utilizing the same irradiation method as in the third embodiment. As a result, the system configuration can be further simplified as compared with that in the third embodiment.

Figure 15:
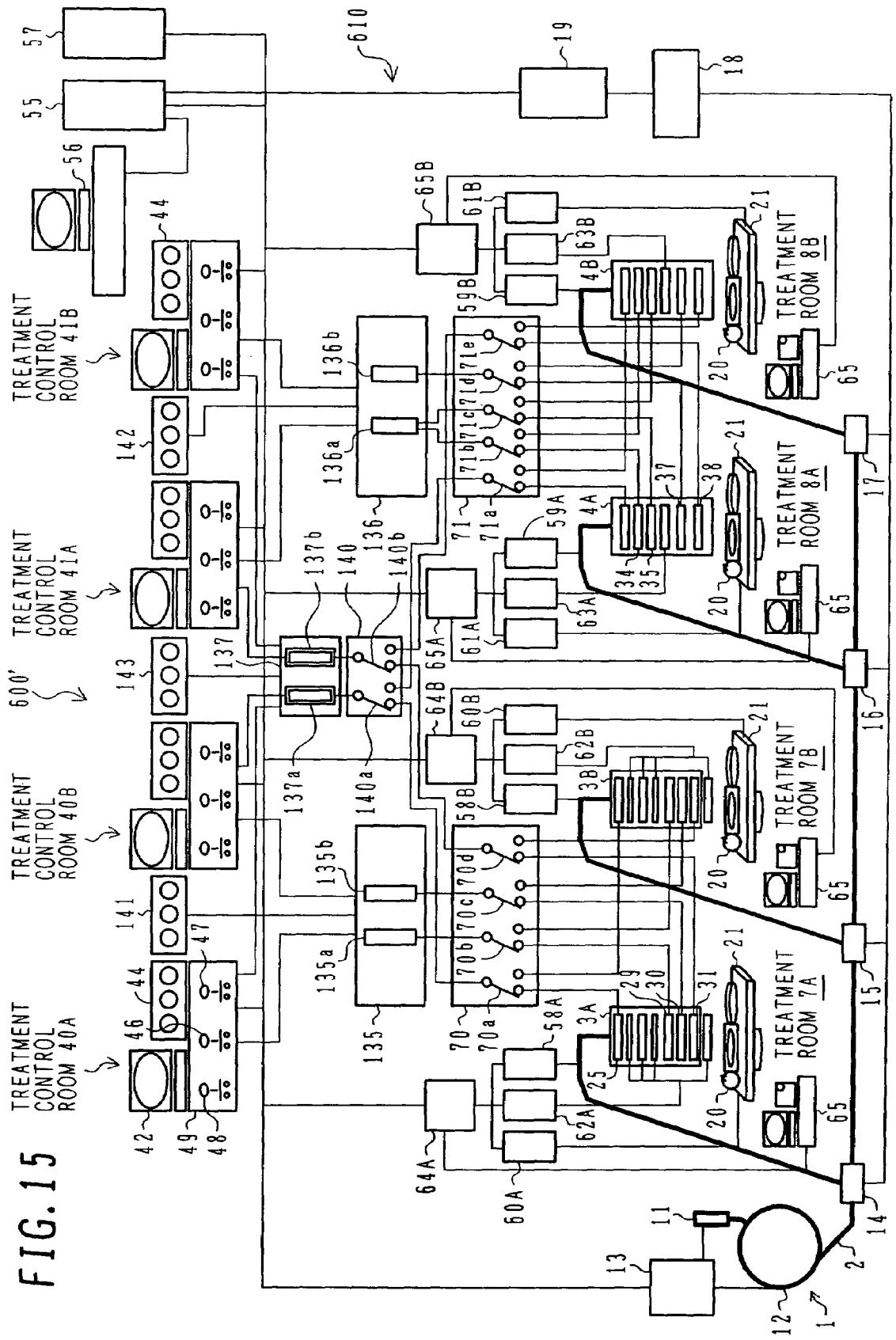
FIG. 15 shows a modification of the particle beam therapy system, shown in FIG. 14, in which a control/monitoring panel is partly shared by a plurality of treatment rooms.

While the above embodiments have been described as providing, for each of the treatment rooms, the display monitor and the operating/monitoring panel which are used for monitoring the beam information, the display monitor and the operating/monitoring panel may also be used in common by a plurality of treatment rooms sharing the beam detection processing/control unit. FIG. 15 shows a modification of the therapy system 600, shown in FIG. 14, in which the control/monitoring panel is partly shared by a plurality of treatment rooms. In FIG. 15, reference numeral 141 denotes an operating/monitoring panel for the treatment rooms utilizing the passive irradiation method, 142 denotes an operating/monitoring panel for the treatment rooms utilizing the scanning irradiation method, and 143 denotes an operating/monitoring panel shared by both the treatment rooms utilizing the passive irradiation method and the scanning irradiation method. To display the item of the beam information (e.g., an operating status) which cannot be shared by a plurality of treatment rooms, however, the operating/monitoring panel is required to be provided in each of the treatment control rooms 40A, 40B, 41A and 41B. Also, the console 49 provided with the irradiation start button 46, the irradiation stop button 47, and the beam request button 48 is required to be provided in each treatment control room from the viewpoint of avoiding a reduction in the operation efficiency of the therapy system.

What is claimed is:

1. A particle beam therapy system for irradiating a charged particle beam to an affected part of the body for treatment, the therapy system comprising:
   a charged particle beam generator for generating the charged particle beam;
   irradiation devices installed respectively in a plurality of treatment rooms and irradiating the charged particle beam, each of said irradiation devices including a plurality of detectors for detecting beam information of the charged particle beam;
   a beam line for selectively transporting the charged particle beam extracted from said charged particle beam generator to the respective irradiation devices in said plurality of treatment rooms, said beam line being controlled to form a beam path for transporting the charged particle beam to the irradiation device in selected one of said plurality of treatment rooms;
   a single monitoring unit arranged for said irradiation devices for monitoring the beam information of the charged particle beam detected by said detectors;
   a first selector for switchably connecting said detectors provided in each of said irradiation devices and said monitoring unit; and
   a first control unit for controlling said first selector such that when said beam path for transporting the charged particle beam to the irradiation device in said selected one of said plurality of treatment rooms is formed, said first selector establishes connection between said detectors provided in the irradiation device in said selected one of said plurality of treatment rooms and said monitoring unit.

2. The particle beam therapy system according to claim 1, further comprising a display unit for displaying the beam state of the charged particle beam in one of said irradiation devices,
   wherein said first selector switchably selects one of said irradiation devices to be displayed by said display unit.

3. The particle beam therapy system according to claim 1, wherein said monitoring unit determines whether the beam information of the charged particle beam detected by said detectors is within an allowable range.

4. The particle beam therapy system according to claim 3, further comprising a second control unit for controlling said charged particle beam generator to stop extraction of the charged particle beam when said monitoring unit determines that the beam information of the charged particle beam exceeds the allowable range.

5. The particle beam therapy system according to claim 4, further comprising a determining unit for determining whether said first selector has established connection with the irradiation device in the selected one of said plurality of treatment rooms.

6. The particle beam therapy system according to claim 5, further comprising a third control unit for controlling said charged particle beam generator to stop extraction of the charged particle beam when said determining unit determines that said first selector has not established connection with the irradiation device in the selected one of said plurality of treatment rooms.

7. The particle beam therapy system according to claim 6, wherein said irradiation devices are constructed as irradiation devices utilizing the irradiation method.

8. The particle beam therapy system according to claim 7, wherein said irradiation devices are constructed as irradiation devices operating in accordance with passive irradiation.

9. The particle beam therapy system according to claim 8, wherein each of said irradiation devices includes, as said detectors, a profile monitor for measuring the centroid and width of the charged particle beam, an energy monitor for measuring energy of the charged particle beam, a flatness monitor for measuring uniformity of the charged particle beam in a direction perpendicular to the direction of travel of the beam, and a dose monitor for measuring dose, and wherein said monitoring unit determines whether the beam information of the charged particle beam detected by said profile monitor, said energy monitor and said flatness monitor is within an allowable range, and whether the dose of the charged particle beam detected by said dose monitor has reached a preset value.

10. The particle beam therapy system according to claim 7, wherein said irradiation devices are constructed as irradiation devices operating in accordance with scanning irradiation.

11. The particle beam therapy system according to claim 10, wherein each of said irradiation devices includes, as said detectors, a profile monitor for measuring the centroid and width of the charged particle beam, a spot position monitor for measuring the centroid and width of the charged particle beam bent by a bending magnet, and a dose monitor for measuring dose, and wherein said monitoring unit determines whether the beam information of the charged particle beam detected by said profile monitor and said spot position monitor is within an allowable range, and whether the dose of the charged particle beam detected by said dose monitor has reached a preset value.

12. The particle beam therapy system according to claim 6, wherein said irradiation devices include irradiation devices utilizing at least two kinds of different irradiation methods.

13. The particle beam therapy system according to claim 12, wherein said irradiation devices are made up of irradiation devices operating in accordance with passive irradiation and scanning irradiation.

14. The particle beam therapy system according to claim 13, wherein each of said irradiation devices includes, as said detectors, a profile monitor for measuring the centroid and width of the charged particle beam and a dose monitor for measuring dose, and wherein said monitoring unit determines whether the beam information of the charged particle beam detected by said profile monitor is within an allowable range, and whether the dose of the charged particle beam detected by said dose monitor has reached a preset value.

15. A particle beam therapy system for irradiating a charged particle beam to an affected part of the body for treatment, the therapy system comprising:
  a charged particle beam generator for generating the charged particle beam;
  irradiation devices installed respectively in a plurality of treatment rooms and irradiating the charged particle beam in a scanning manner, each of said irradiation devices including scanning magnets;
  a beam line for selectively transporting the charged particle beam extracted from said charged particle beam generator to the respective irradiation devices in said plurality of treatment rooms, said beam line being controlled to form a beam path for transporting the charged particle beam to the irradiation device in selected one of said plurality of treatment rooms;
  a single scan control unit arranged for said irradiation devices for controlling a scanning of the charged particle;
  a selector for switchably connecting said scanning magnets provided in each of said irradiation devices and said scan control unit; and
  a control unit for controlling said selector such that when said beam path for transporting the charged particle beam to the irradiation device in said selected one of said plurality of treatment rooms is formed, said selector establishes connection between said scanning magnets provided in the irradiation device in the selected one of said plurality of treatment rooms and said scan control unit.

16. The particle beam therapy system according to claim 15, wherein said scan control unit controls a current value of said scanning magnet for scanning the charged particle beam.

17. A control system for a particle beam therapy system having irradiation devices installed respectively in a plurality of treatment rooms for irradiating a charged particle beam, each of said irradiation devices including a plurality of detectors for detecting beam information of the charged particle beam and beam line for selectively transporting the charged particle beam to the respective irradiation devices in said plurality of treatment rooms, the control system comprising:
  a beam line control unit for controlling said beam line such that a beam path for transporting the charged particle beam to the irradiation device in selected one of said plurality of treatment rooms is formed;
  a single monitoring unit arranged for said irradiation devices for monitoring the beam information of the charged particle beam detected by said detectors;
  a selector for switchably connecting said detectors provided in each of said irradiation devices and said monitoring unit; and
  a control unit for controlling said selector such that when said beam path for transporting the charged particle beam to the irradiation device in said selected one of said plurality of treatment rooms is formed, said selector establishes connection between said detectors provided in the irradiation device in the selected one of said plurality of treatment rooms and said monitoring unit.

18. The control system for the particle beam therapy system according to claim 17, wherein said monitoring unit determines whether the beam information of the charged particle beam detected by said detectors is within an allowable range.

19. A control system for a particle beam therapy system having irradiation devices installed respectively in a plurality of treatment rooms for irradiating a charged particle beam in scanning manner, each of said irradiation devices including scanning magnets and a beam line for selectively transporting the charged particle beam to the respective irradiation devices in said plurality of treatment rooms, the control system comprising:
  a beam line control unit for controlling said beam line such that a beam path for transporting the charged particle beam to the irradiation device in selected one of said plurality of treatment rooms is formed;
  a single scan control unit arranged for said irradiation devices for controlling a scanning of the charged particle beam;

a selector for switchably connecting said scanning magnets provided in each of said irradiation devices and said scan control unit; and a control unit for controlling said selector such that when said beam path for transporting the charged particle beam to the irradiation device in said selected one of said plurality of treatment rooms is formed, said selector establishes connection between said scanning magnets provided in the irradiation device in the selected one of said plurality of treatment rooms and said scan control unit.

20. The particle beam therapy system according to claim 1, wherein said beam line includes switching magnets provided correspondingly to said irradiation devices; and said particle beam therapy system further comprises a fourth control unit for exiting the switching magnet corresponding to the irradiation device in said selected one of said plurality of treatment rooms by switching a power supply for said switching magnet so as to form said beam path for transporting the charged particle beam to the irradiation device in said selected one of said plurality of treatment rooms and then deliver a first signal when the formation of said beam path is completed; and said first control unit delivers a second signal to said first selector based on said first signal delivered by said fourth control unit thereby to control said first selector such that said first selector establishes connection between said detectors provided in the irradiation device in said selected one of said plurality of treatment rooms and said monitoring unit.

* * * * *